US008497064B2

(12) United States Patent
McGall et al.

(10) Patent No.: US 8,497,064 B2
(45) Date of Patent: *Jul. 30, 2013

(54) NUCLEIC ACID LABELLING COMPOUNDS

(75) Inventors: Glenn H. McGall, Palo Alto, CA (US); Anthony D. Barone, San Jose, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/286,870

(22) Filed: Nov. 1, 2011

(65) Prior Publication Data

US 2012/0053336 A1 Mar. 1, 2012

Related U.S. Application Data

(60) Continuation of application No. 12/892,531, filed on Sep. 28, 2010, now Pat. No. 8,076,072, which is a division of application No. 12/163,528, filed on Jun. 27, 2008, now Pat. No. 8,026,057, which is a division of application No. 10/097,113, filed on Mar. 12, 2002, now Pat. No. 7,468,243.

(60) Provisional application No. 60/275,202, filed on Mar. 12, 2001.

(51) Int. Cl.
*C12Q 1/68* (2006.01)
*C07D 239/02* (2006.01)

(52) U.S. Cl.
USPC ............ 435/6; 536/23.1; 536/25.1; 544/320; 549/430

(58) Field of Classification Search
USPC .................... 435/6; 536/23.1, 25.1; 544/320, 544/321; 549/430
See application file for complete search history.

(56) References Cited

U.S. PATENT DOCUMENTS

| 3,352,849 A | 11/1967 | Shen |
|---|---|---|
| 3,817,837 A | 6/1974 | Rubenstein et al. |
| 3,850,752 A | 11/1974 | Schuurs et al. |
| 3,891,623 A | 6/1975 | Vorbruggen et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,594,339 A | 6/1986 | Lopez et al. |
| 4,981,783 A | 1/1991 | Augenlicht |
| 4,997,928 A | 3/1991 | Hobbs, Jr. |
| 5,002,867 A | 3/1991 | Macevicz |
| 5,143,854 A | 9/1992 | Pirrung et al. |
| 5,151,507 A | 9/1992 | Hobbs, Jr. et al. |
| 5,202,231 A | 4/1993 | Drmanac et al. |
| 5,242,796 A | 9/1993 | Prober et al. |
| 5,262,536 A | 11/1993 | Hobbs, Jr. |
| 5,324,633 A | 6/1994 | Fodor et al. |
| 5,332,666 A | 7/1994 | Prober et al. |
| 5,422,241 A | 6/1995 | Goldrick et al. |
| 5,424,186 A | 6/1995 | Fodor et al. |
| 5,445,934 A | 8/1995 | Fodor et al. |
| 5,543,292 A | 8/1996 | Imai et al. |
| 5,571,639 A | 11/1996 | Hubbell et al. |
| 5,608,063 A | 3/1997 | Hobbs, Jr. et al. |
| 5,744,305 A | 4/1998 | Fodor et al. |
| 6,174,998 B1 | 1/2001 | Muhlegger et al. |
| 6,211,158 B1 | 4/2001 | Seela et al. |
| 6,864,059 B2 | 3/2005 | McGall et al. |
| 7,468,243 B2 * | 12/2008 | McGall et al. ............... 435/6.16 |

FOREIGN PATENT DOCUMENTS

| DE | 19509038 | 9/1996 |
|---|---|---|
| EP | 132621 | 2/1985 |
| EP | 159719 | 10/1985 |
| EP | 252683 | 1/1988 |
| EP | 266787 | 5/1988 |
| EP | 320308 | 6/1989 |
| EP | 322311 | 6/1989 |
| EP | 336731 | 10/1989 |
| EP | 535242 | 4/1993 |
| EP | 717113 | 6/1996 |
| EP | 7210016 | 7/1996 |
| FR | 2551442 | 3/1985 |
| JP | 61 109797 | 5/1986 |
| WO | WO 89/10977 | 11/1989 |
| WO | WO 90/00626 | 1/1990 |
| WO | WO 90/03370 | 4/1990 |
| WO | WO 90/04652 | 5/1990 |
| WO | WO 90/15070 | 12/1990 |
| WO | WO 92/02258 | 2/1992 |
| WO | WO 92/10092 | 6/1992 |
| WO | WO 92/10588 | 6/1992 |
| WO | WO 93/16094 | 8/1993 |
| WO | WO 93/17126 | 9/1993 |
| WO | WO 95/00530 | 1/1995 |

(Continued)

OTHER PUBLICATIONS

Akita, Y. et al.,"Cross-Coupling Reaction of Chloropyrazines with Acetylenes," Chemical & Pharmaceutical Bulletin, 34, 4 A.D., pp. 1447-1458, (2001).

Aoyagi, Mitsutoshi et al. "Nucleosides and nucleotides. 115. Synthesis of 3-alkyl-3-deazainosines via palladium-catalyzed intramolecular cyclization: A new conformational lock wi," Tetrahedron Letters, 34, Jan. 1, 1993, pp. 103-106.

Avila, J. L. et al. "Biological action of pyrazolopyrimidine derivatives against *Trypanosoma cruzi*. Studies in vitro and in vivo," Comp Biochem.Physiol C., 86, 1987, pp. 49-54.

Barringer, K. J. et al. "Blunt-end and single-strand ligations by *Escherichia coli* ligase: influence on an in vitro amplification scheme," Gene, 89, Apr. 30, 1990, pp. 117-122.

Basnak, I. et al. "Some 6-aza-5-substituted-2'-deoxyuridines show potent and selective inhibition of herpes simplex virus type 1 thymidine kinase," Nucleosides Nucleotides, 17, Jan. 1998, pp. 187-206.

(Continued)

*Primary Examiner* — Paul V. Ward
(74) *Attorney, Agent, or Firm* — Affymetrix, Inc.

(57) ABSTRACT

Nucleic acid labeling compounds are disclosed. The compounds are synthesized by condensing a heterocyclic derivative with a cyclic group (e.g. a ribofuranose derivative). The labeling compounds are suitable for enzymatic attachment to a nucleic acid, either terminally or internally, to provide a mechanism of nucleic acid detection.

26 Claims, 11 Drawing Sheets

FOREIGN PATENT DOCUMENTS

| | | |
|---|---|---|
| WO | WO 95/04594 | 2/1995 |
| WO | WO 95/04833 | 2/1995 |
| WO | WO 95/04834 | 2/1995 |
| WO | WO 95/11995 | 5/1995 |
| WO | WO 95/20681 | 8/1995 |
| WO | WO 95/30774 | 11/1995 |
| WO | WO 95/35505 | 12/1995 |
| WO | WO 96/28460 | 9/1996 |
| WO | WO 97/10365 | 3/1997 |
| WO | WO 97/27317 | 7/1997 |
| WO | WO 97/28176 | 8/1997 |
| WO | WO 97/29212 | 8/1997 |
| WO | WO 97/39120 | 10/1997 |
| WO | WO 98/11104 | 3/1998 |
| WO | WO 00/06771 | 2/2000 |

OTHER PUBLICATIONS

Beabealashvilli, Robert S. et al. "Nucleoside 5'-triphosphates modified at sugar residues as substrates for calf thymus terminal deoxynucleotidyl transferase and for AMV reverse transcriptase," Biochimica et Biophysica Acta (BBA)—Gene Structure and Expression, 868, Nov. 13, 1986, pp. 136-144.

Bergeron, et al.,"Reagents for the Stepwise Functionalization of Spermine," J.Org.Chem., 53, 1998, pp. 3108-3111.

Bergstrom, D. E.,"Design and Synthesis of Heterocyclic Carboxamides as Natural Nucleic Acid Base Mimics," Nucleosides Nucleotides, 15, 1996, pp. 59-68.

Bobek, M.,"Nucleic Acids Components and their Analogues. XCVII Synthesis of 5-Hydroxmethyl-6-Aza-2'- Deoxyuridine and 5-Hydroxymethyl-6-Aza-2'-Deoxycytidine," Collection Czechoslov.Chem.Commun., 32, 2008, pp. 3581-3586.

Brody, R. S. et al. "The purification of orotidine-5'-phosphate decarboxylase from yeast by affinity chromatography," J.Biol.Chem., 254, May 25, 1979, pp. 4238-4244.

Broude, N. E. et al. "Enhanced DNA sequencing by hybridization," Proc.Natl.Acad.Sci.U.S.A, 91, Apr. 12, 1994, pp. 3072-3076.

Canard, B. et al. "Catalytic editing properties of DNA polymerases," Proc.Natl.Acad.Sci.U.S.A, 92, Nov. 21, 1995, pp. 10859-10863.

Cech, D.,"New Approaches Toward the Synthesis of Non-Radioactively Labelled Nucleoside Triphosphates as Terminators for DNA Sequencing," Collection Czechoslov.Chem.Commun., 61, 1996, pp. S297-S300.

Chee, M. et al. "Accessing genetic information with high-density DNA arrays," Science, 274, Oct. 25, 1996, pp. 610-614.

Chernetskii, V. P.,"Anomalous Nucleosides and Related Compounds XIV. Derivatives of 6-Azacytidine," Chemical Abstracts, 74, 1971.

Chidgeavadez, Z. G.,"2', 3'-Dideoxy-3' Amnionucleoside 5'-Triphosphates are the terminators of DNA Synthesis Catalyzed by DNA Polymerases," Nucleic Acids Res., 12, 1984, pp. 1671-1686.

Chu,"General Synthesis of 2', 3'-dideoxynucleosides and 2',3' didehydro-2',3'-dideoxynucleosides," J.Org.Chem., 54, 1989, pp. 2217-2225.

Cottam, H. B. et al. "New adenosine kinase inhibitors with oral antiinflammatory activity: synthesis and biological evaluation," J.Med.Chem., 36, Oct. 29, 1993, pp. 3424-3430.

Curriden, M.,"A New Evidence Tool—First use of Mitochondrial DNA Test in a U.S. Criminal Trial," ABA Journal, Nov. 1996, 1 pg.

Dansher, J. et al.,"Autometallographic Silver Amplification of Colloidal Gold," J.Hisotech, 15, 1993, pp. 201-207.

Depelley, J. et al.,"New Non—Aromatic Triazinic Nucleosides: Synthesis and Antiretroviral Evaluation of Beta-Ribosylamine Nucleoside Analogs," Nucleosides & Nucleotides, 15, 1996, pp. 995-1008.

Dueholm, et al. "2,3-dideoxy-furanoses in convergent synthesis of 2', 3'-dideoxy nucleosides", Synthesis, (1992), pp. 1-22.

Edo, K. et al.,"Studies on Pyrimidine Derivatives IX Coupling Reaction of Mono-Substituted Acetylenes with Iodopyrimidines," Chemical & Pharmaceutical Bulletin, 26, 1978, pp. 3843-3850.

Eggers, M. et al. "A microchip for quantitative detection of molecules utilizing luminescent and radioisotope reporter groups," Biotechniques, 17, Sep. 1994, pp. 516-525.

Feldman, W. et al. "Gray code masks for sequencing by hybridization," Genomics, 23, Sep. 1, 1994, pp. 233-235.

Fodor, S. P. et al. "Light-directed, spatially addressable parallel chemical synthesis," Science, 251, Feb. 15, 1991, pp. 767-773.

Freskos, J. N.,"Synthesis of 2'-Deoxypyrimidine Nucleosides Via Copper (I) Iodine Catalysis," Nucleosides & Nucleotides, 8, 1989, pp. 549-555.

Galushko, S. V. et al. "Relationship between retention parameters in reversed-phase high-performance liquid chromatography and antitumour activity of some pyrimidine bases and nucleosides," Journal of Chromatography A, 547, Jun. 28, 1991, pp. 161-166.

Galushko, S. V.,"Reversed—phase HPLC of N4-and O'-Derivatives of 6-azacytidine," Chemical Abstracts, 111, 1990.

Grzybowski, J. et al. "Synthesis and antibody-mediated detection of oligonucleotides containing multiple 2,4-dinitrophenyl reporter groups," Nucleic Acids Res., 21, Apr. 25, 1993, pp. 1705-1712.

Guatelli, J. C. et al. "Isothermal, in vitro amplification of nucleic acids by a multienzyme reaction modeled after retroviral replication," Proc.Natl.Acad.Sci.U.S.A, 87, Mar. 1990, pp. 1874-1878.

Hamilton, H. et al.,"C4-Substituted 1-beta-D-Ribofuranosylpyrazolo[3,4-d]Pyrimidines as Adenosine Agonist Analogues," J.Med.Chem., 26, 1993, pp. 1601-1606.

Herrlein, et. al.,"57.3'-Amino-Modified Nucleotides Useful as Potent Chain Terminators for Current DNA Sequencing Methods," Helvecta Chemica Acta, 77, 1994, pp. 586-596.

Hobbs, Jr. F. W. et al.,"Palladium-Catalyzed Synthesis of Alkynylamino Nucleosides. A Universal Linker for Nucleic Acids," J.Org.Chem., 54, 1989, pp. 3420-3422.

Hoheisel, J. D.,"Application of hybridization techniques to genome mapping and sequencing," Trends Genet., 10, Mar. 1994, pp. 79-83.

Holy,"Oligonucleotidic Compounds. XVII Synthesis of Oligonucleotides Containing 6-Azauriding ad 6-Azacytidine," Collection Czechoslov.Chem.Commun., 32, 1967, pp. 2980-2997.

Izuta, S.,"Chain Termination with Sugar-Modified Nucleotide Analogs in the DNA Synthesis by DNA Polymerase Y," Nucleosides Nucleotides, 15, 1996, pp. 683-692.

Johnson, W. T. et al. "The synthesis and stability of oligodeoxyribonucleotides containing the deoxyadenosine mimic 1-(2'-deoxy-beta-D-ribofuranosyl)imidazole-4-carboxamide," Nucleic Acids Res., 25, Feb. 1, 1997, pp. 559-567.

Kallioniemi, A. et al. "Comparative genomic hybridization for molecular cytogenetic analysis of solid tumors," Science, 258, Oct. 30, 1992, pp. 818-821.

Khrapko, K. R. et al. "An oligonucleotide hybridization approach to DNA sequencing," FEBS Lett., 256, Oct. 9, 1989, pp. 118-122.

Kohler, P.,"Synthese von Desoxyribonucleosid-Monophosphaten und-Triphosphaten mit 2 (1 H)-Pyrimidinon, 2 (1 H)-Pyridinon and 4-Amino-2 (1 H)-Pyridinon als Basen," Helvecta Chemica Acta, 63, 1980, pp. 2488-2494.

Kutateladze, Tamata et al. "3'-Deoxy-3'-aminonucleoside 5'-triphosphates—Terminators of RNA synthesis, catalyzed by DNA-dependent RNA polymerase from Escherichia coli," FEBS Letters, 153, Mar. 21, 1983, pp. 420-426.

Kwoh, D. Y. et al. "Transcription-based amplification system and detection of amplified human immunodeficiency virus type 1 with a bead-based sandwich hybridization format," Proc.Natl.Acad.Sci.U.S.A, 86, Feb. 1989, pp. 1173-1177.

Landegren, U. et al. "A ligase-mediated gene detection technique," Science, 241, Aug. 26, 1988, pp. 1077-1080.

Langer, P. R. et al. "Enzymatic synthesis of biotin-labeled polynucleotides: novel nucleic acid affinity probes," Proc.Natl.Acad.Sci.U.S.A, 78, Nov. 1981, pp. 6633-6637.

Lazurkevich, Z. V.,"Growth Activity of 6-Substituted Azauracils," Chemical Abstracts, 102, 1985.

Le Bec, C.,"Derivatives of Imidazole-4-Carboxamide as Substrates for Various DNA Polymerases," Nucleosides Nucleotides, 167, 1997, pp. 1301-1302.

Lennon, G. G. et al. "Hybridization analyses of arrayed cDNA libraries," Trends Genet., 7, Oct. 1991, pp. 314-317.

Lipshutz, R. J. et al. "Using oligonucleotide probe arrays to access genetic diversity," Biotechniques, 19, Sep. 1995, pp. 442-447.

Lockhart, D. J. et al. "Expression monitoring by hybridization to high-density oligonucleotide arrays," Nat.Biotechnol., 14, Dec. 1996, pp. 1675-1680.

Ludwig, "Rapid and efficient Synthesis of Nucleoside 5'-0-(1-Thiotriphosphates), 5'-triphosphates and 2', 3'-Cyclophosphorothioates using 2-chloro-4H-1,3,2-Benzodioxaphosphorin-4-one," J.Org. Chem., 54, 1989, pp. 631-635.

Mikkelsen, T. et al. "Genetics of the malignant progression of astrocytoma," J.Cell Biochem., 46, May 1991, pp. 3-8.

Mirkin, C. A. et al. "A DNA-based method for rationally assembling nanoparticles into macroscopic materials," Nature, 382, Aug. 15, 1996, pp. 607-609.

Misura, K., "Biotinyl and Phosphotyrosinyl Phosporamidite Derivatives useful in the Incorporation of Multiple Reporter Groups on Synthetic Oligonucleotides," Nucleic Acids Res., 18, 1990, pp. 4345-4354.

Mitchell, W. L. et al. "Synthesis and antiviral properties of 5-(2-substituted vinyl)6-aza-2'-deoxyuridines," J.Med.Chem., 29, May 1986, pp. 809-816.

Nelson, P. S. et al. "Oligonucleotide labeling methods. 3. Direct labeling of oligonucleotides employing a novel, non-nucleosidic, 2-aminobutyl-1,3-propanediol backbone," Nucleic Acids Res., 20, Dec. 11, 1992, pp. 6253-6259.

Niedballa, U. et al. "A general synthesis of N-glycosides. I. Synthesis of pyrimidine nucleosides," J.Org.Chem., 39, Dec. 13, 1974, pp. 3654-3660.

Nishida, Masakazu et al. "Facile perfluoroalkylation of uracils and uridines at the C-5 position," Journal of Fluorine Chemistry, 63, Jul. 1993, pp. 43-52.

Ohsawa, A., "Alkynylation of Halopyridazines and their N-Oxides," Chemical & Pharmaceutical Bulletin, 28, 1980, pp. 3488-3493.

Pankiewicz, K. W. et al. "Nucleosides-126 : Selective methylation of the C-nucleoside, [psi]-isocytidine and its 2$-deoxy analog. Synthesis of 1-methyl, 3-methyl and 4-o-methyl derivatives," Tetrahedron, 40, 1984, pp. 33-38.

Pedersen, E. B. et al. "2,3-Dideoxyfuranoses in convergent syntheses of 2',3'-dideoxy nucleoside," Antiviral Research, 15, Apr. 1991, pp. 56-56.

Petrie, C. R. et al. "A novel biotinylated adenylate analogue derived from pyrazolo[3,4-d]pyrimidine for labeling DNA probes," Bioconjug.Chem., 2, Nov. 1991, pp. 441-446.

Pevzner, P. A. et al. "Improved chips for sequencing by hybridization," J.Biomol.Struct.Dyn., 9, Oct. 1991, pp. 399-410.

Pirrung, Michael C. et al. "A convenient procedure for the deprotection of silylated nucleosides and nucleotides using triethylamine trihydrofluoride," Bioorganic & Medicinal Chemistry Letters, 4, Jun. 9, 1994, pp. 1345-1346.

Pochet, S. et al. "Synthesis and enzymatic polymerisation of 5-amino-1-(2'-deoxy-beta-D-ribofuranosyl)imidazole-4-carboxamide-5'-triphosphate," Nucleic Acids Res., 18, Dec. 11, 1990, pp. 7127-7131.

Pochet, Sylvie, et al., Ambiguous Base Pairing of 1-(2-Deoxy-D-Ribofuranosyl)imidazole-4-carboxamide During PCR, Nucleosides, Nucleotides and Nucleic Acids, 1997, 16(7): pp. 1749-1752.

Pochet., "Enzymatic Synthesis of 1-(2-deoxy-beta-D-ribofuranosyl) Imidazole-4-Carboxamide, a Simplified DNA Building Block," Bioorganic & Medicinal Chemistry Letters, 5, 1995, pp. 1679-1684.

Prober, J. M. et al. "A system for rapid DNA sequencing with fluorescent chain-terminating dideoxynucleotides," Science, 238, Oct. 16, 1987, pp. 336-341.

Prystas, M., "Nucleic Acids Components and their Analogues. CXXI. Glycosylation of 6-Azathymine by the Silylation Process," Collection Czechoslov.Chem.Commun., 34, 1969, pp. 1104-1107.

Ramzaeva, N., et al., "Oligonucleotides Functionalized by Fluorescein and Rhodamine Dyes: Michael Addition of Methyl Acrylate to 2'-Deoxypseudouridine," Helvetica Chimica Acta, 83 2000, pp. 1108-1126.

Rideout, J. L. et al. "Pyrazolo[3,4-d]pyrimidine ribonucleosides as anticoccidials. 2. Synthesis and activity of some nucleosides of 4-(alkylamino)-1H-pyrazolo[3, 4-d]pyrimidines," J.Med.Chem., 25, Sep. 1982, pp. 1040-1044.

Robins, "Nucleic Acid Related Compounds, 42. A General Procedure for the Efficient Deoxygenation of Secondary Alcohols, Regiospecific and Stereoselective Conversation of Ribonucleosides to 2' Synthesis and Activity of Some Nucleosides of 4-(Alkylamino)-1H-Pyrazolo [3,4-d Pyrimidines," Journal of American Chemical Society, 105, 983, pp. 4059-4065.

Robins, "Potential Purine Antagonists. I. Synthesis of some 4,6-Substituted Pyrazolo [3,4-d] pyrimidines," Journal of American Chemical Society, 78, 1995, pp. 784-790.

Rosemeyer, H., "Stereoelectronic Effects of Modified Purines on the Sugar Conformation of Nucleosides and Fluorescence Properties," Nucleosides Nucleotides, 16, 1997, pp. 821-828.

Sala, M. et al. "Ambiguous base pairing of the purine analogue 1-(2-deoxy-beta-D-ribofuranosyl)-imidazole-4-carboxamide during PCR," Nucleic Acids Res., 24, Sep. 1, 1996, pp. 3302-3306.

Sambrook, "Bacteriophage T4 RNA Ligase (Bactriophage T4-Infected E. Coli)," Molecular Cloning: A Laboratory Manual, 2nd edition, 1989, pp. 5.66-5.69.

Schena, M. et al. "Parallel human genome analysis: microarray-based expression monitoring of 1000 genes," Proc.Natl.Acad.Sci.U. S.A, 93, Oct. 1, 1996, pp. 10614-10619.

Seela, F., "131 8-Aza 7-Deaza-2'-deoxyguanosine: Phosphoramidite Synthesis and Properties of Ocanucleotides," Helvecta Chemica Acta, 71, 1988, pp. 1191-1198.

Seela, F., "193. 8 Aza-7 deazaadenine N8-and N9-(Beta-D-2'-Deoxyribfuranosides): Building Blocks for Automated DNA Synthesis and Properties of Oligodeoxyribonucleotides," Helvecta Chemica Acta, 71, 1988, pp. 1813-1823.

Seela, F., "Alternating d(G-C)3 and d (C-G)3 Hexanucletides Containing 7-Deaza-2'-Deoxyguanosine in Place of dG," Nucleic Acids Res., 17, 1989, pp. 901-910.

Seela, F., "Synthesis of 7-Alkynated 8-Aza-7-Deaza-2'-Deoxyadenosines via the Pd-Catalysed Cross-Coupling Reaction," J.Chem.Society, 1998, pp. 3233-3239.

Seela, F., "Synthesis of Oligonucleotides Containing Pyrazolo [3,4-d] Pyrimidines: The Influence of 7-Substituted 8-Aza-7-Deazaadenines on the Duplex Structure and Stability," J.Chem.Society, 1999, pp. 479-488.

Southern, E. M. et al. "Analyzing and comparing nucleic acid sequences by hybridization to arrays of oligonucleotides: evaluation using experimental models," Genomics, 13, Aug. 1992, pp. 1008-1017.

Southern, E. M. et al. "Arrays of complementary oligonucleotides for analysing the hybridisation behaviour of nucleic acids," Nucleic Acids Res., 22, Apr. 25, 1994, pp. 1368-1373.

Stille, J. K., "Stereospecific Palladium-Catalyzed Coupling Reactions of Vinyl Iodides with Acetylenic Tin Reagents," Journal of American Chemical Society, 109, Apr. 1, 1987, pp. 2138-2152.

Stimpson, D. I. et al. "Real-time detection of DNA hybridization and melting on oligonucleotide arrays by using optical wave guides," Proc.Natl.Acad.Sci.U.S.A, 92, Jul. 3, 1995, pp. 6379-6383.

Tanji, K., "Studies on Pyrimidine Derivatives XXVII. Synthesis of 2-and 4-Pyrimidinyl Ketones by Means of the Hydration of Alkynylprimidines," Chemical & Pharmaceutical Bulletin, 30, May 1982, pp. 1865-1867.

Theisen, P. et al. "Fluorescent dye phosphoramidite labelling of oligonucleotides," Nucleic Acids Symp.Ser., 1992, pp. 99-100.

Uhlenbeck, Olke C. et al. "2 T4 RNA Ligase,", vol. 15, 1982, pp. 31-58.

Wages, John M. et al. "High-Performance Liquid Chromatography Analysis of PCR Products,", 1995, pp. 140-153.

Wang, D. G. et al. "Large-scale identification, mapping, and genotyping of single-nucleotide polymorphisms in the human genome," Science, 280, May 15, 1998, pp. 1077-1082.

Wojczewski, C.,"Synthesis and Application of 3'-Amino-Dye-Terminators for DNA Sequencing," Nucleosides & Nucleotides, 16, 1997, pp. 751-754.

Wu, Dan Y. et al. "The ligation amplification reaction (LAR)—Amplification of specific DNA sequences using sequential rounds of template-dependent ligation," Genomics, 4, May 1989, pp. 560-569.

Yu, H. et al. "Cyanine dye dUTP analogs for enzymatic labeling of DNA probes," Nucleic Acids Res., 22, Aug. 11, 1994, pp. 3226-3232.

Zhu, Z. et al. "Directly labeled DNA probes using fluorescent nucleotides with different length linkers," Nucleic Acids Res., 22, Aug. 25, 1994, pp. 3418-3422.

No Author, "Wikipedia, the free encyclopedia"[online]. Wikimedia Foundation Inc. St. Petersburg, GL, Mar. 2, 2005, pp. 4, [retrieved on Mar. 2, 2005]. Retreived from the internet<http:en.wikipedia.org/wiki/chemistry#Laws>.

* cited by examiner fluorescein and biotin labeled N1-ψCTP

6 R = carboxyfluroscein
7 R = CO(CH$_2$)$_2$O(CH$_2$)$_2$O(CH$_2$)$_2$O(CH$_2$)$_2$O(CH2)2NH-biotin fluorescein and biotin labeled N1-ψCTP

6 R = carboxyfluroscein
7 R = CO(CH$_2$)$_2$O(CH$_2$)$_2$O(CH$_2$)$_2$O(CH$_2$)$_2$O(CH2)2NH-biotin 10 R = carboxyfluroscein
11 R = CO(CH₂)₂O(CH₂)₂O(CH₂)₂O(CH₂)₂O(CH2)2NH-biotin 14 R = carboxyfluroscein
15 R = CO(CH$_2$)$_2$O(CH$_2$)$_2$O(CH$_2$)$_2$O(CH$_2$)$_2$O(CH2)2NH-biotin 20 R = carboxyfluroscein
21 R = CO(CH$_2$)$_2$O(CH$_2$)$_2$O(CH$_2$)$_2$O(CH$_2$)$_2$O(CH2)2NH-biotin

NUCLEIC ACID LABELLING COMPOUNDS

CROSS REFERENCE TO RELATED APPLICATIONS

This application is a divisional application of U.S. patent application Ser. No. 12/163,528, filed Jun. 27, 2008, which is a divisional application of U.S. patent application Ser. No. 10/097,113, filed Mar. 12, 2002, now U.S. Pat. No. 7,468,243, which claims priority from U.S. Provisional Patent Application Ser. No. 60/275,202, filed on Mar. 12, 2001. Each of these applications is incorporated herein in its entirety by reference for all purposes.

STATEMENT OF RIGHTS TO INVENTIONS MADE UNDER FEDERALLY SPONSORED RESEARCH

This invention was made with Government support under contract 70NANB5H1031 awarded by the Advanced Technology Program of the National Institute of Standards and Technology. The Government has certain rights in this invention.

BACKGROUND OF THE INVENTION

Gene expression in diseased and healthy individuals is oftentimes different and characterizable. The ability to monitor gene expression in such cases provides medical professionals with a powerful diagnostic tool. This form of diagnosis is especially important in the area of oncology, where it is thought that the overexpression of an oncogene, or the underexpression of a tumor suppressor gene, results in tumorogenesis. See Mikkelson et al. *J. Cell. Biochem.* 1991, 46, 3-8.

One can indirectly monitor gene expression, for example, by measuring a nucleic acid (e.g., mRNA) that is the transcription product of a targeted gene. The nucleic acid is chemically or biochemically labeled with a detectable moiety and allowed to hybridize with a localized nucleic acid probe of known sequence. The detection of a labeled nucleic acid at the probe position indicates that the targeted gene has been expressed. See, e.g., International Application Publication Nos. WO 97/27317, WO 92/10588 and WO 97/10365.

The labeling of a nucleic acid is typically performed by covalently attaching a detectable group (label) to either an internal or terminal position. Scientists have reported a number of detectable nucleotide analogues that have been enzymatically incorporated into an oligo- or polynucleotide. Langer et al. for example, disclosed analogues of dUTP and UTP that contain a covalently bound biotin moiety. *Proc. Natl. Acad. Sci. USA* 1981, 78, 6633-6637. The analogues, shown below, possess an allylamine linker arm that is attached to the C-5 position of the pyrimidine ring. The dUTP and UTP analogues, wherein R is H or OH, were incorporated into a polynucleotide.

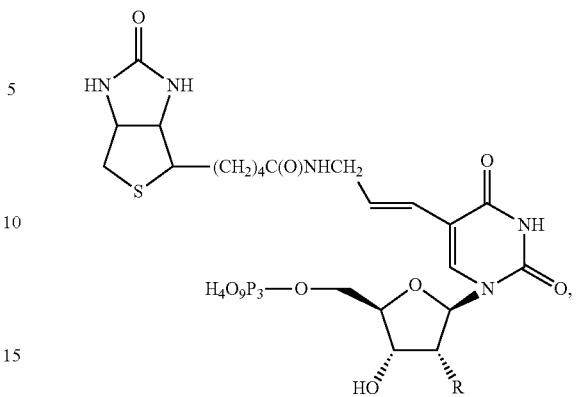

Petrie et al. disclosed a dATP analogue, 3-[5-[(N-biotinyl-6-aminocaproyl)-amino]pentyl]-1-(2-deoxy-β-D-erythro-pentofuranosyl)-1H-pyrazolo[3,4-d]pyrimidin-4-amine-5'-triphosphate. *Bioconjugate Chem.* 1991, 2, 441-446. The analogue, shown below, is modified at the 3-position with a linker arm that is attached to a biotin moiety. Petrie et al. reported that the compound wherein R is biotin is incorporated into DNA by nick translation.

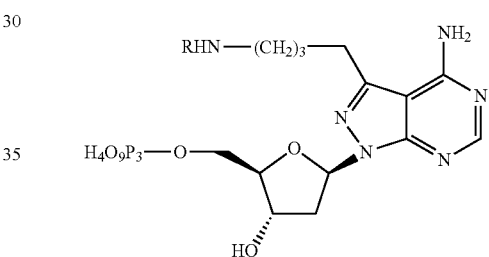

Prober et al. disclosed a set of four dideoxynucleotides, each containing a succinylfluorescein dye. *Science* 1987, 238, 336-341. The dideoxynucleotides, one of which is shown below, were enzymatically incorporated into an oligonucleotide through a template directed extension of a primer. The compounds provided for a DNA sequencing method based on gel migration.

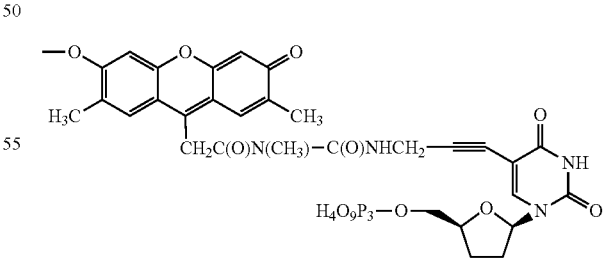

Herrlein et al. disclosed modified nucleoside trisphosphates of the four DNA bases. *Helv. Chim. Acta* 1994, 77, 586-596. The compounds, one of which is shown below, contain a 3'-amino group containing radioactive or fluorescent moieties. Herrlein et al. further described the use of the nucleoside analogues as DNA chain terminators.

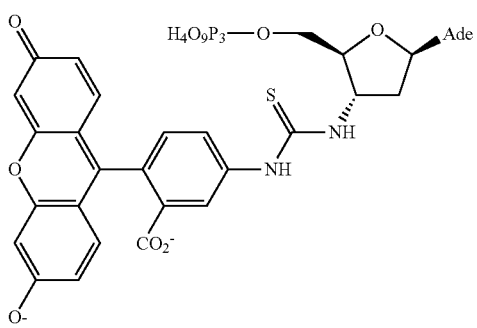

Cech et al. disclosed 3'-amino-functionalized nucleoside triphosphates. *Collect. Czech. Chem. Commun.* 1996, 61, S297-S300. The compounds, one of which is shown below, contain a fluorescein attached to the 3'-position through an amino linker. Cech et al. proposed that the described functionalized nucleosides would be useful as terminators for DNA sequencing.

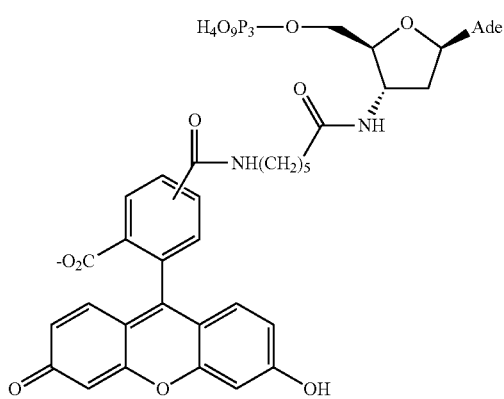

The development of novel nucleic acid labeling compounds that are effectively incorporated into a nucleic acid to provide a readily detectable composition would benefit genetic analysis technologies. It would aid, for example, in the monitoring of gene expression and the detection and screening of mutations and polymorphisms. Such a compound should be suitable for enzymatic incorporation into a nucleic acid. Furthermore, the nucleic acid to which the labeling compound is attached should maintain its ability to bind to a probe, such as a complementary nucleic acid.

Although nucleic acid labeling compounds for use as coupling agents for probes are available there is a continuing need for additional compounds that are more efficient labeling compounds. There also exists a need for compounds that have increased solubility. This will make the compounds more useful for monitoring gene expression.

SUMMARY OF THE INVENTION

The present invention relates to nucleic acid labeling compounds. More specifically, the invention provides compounds containing a detectable moiety. The invention also provides methods of making these compounds. It further provides methods of attaching the compounds to a nucleic acid. The nucleic acid labeling compounds or the present invention are effectively incorporated into a nucleic acids to provide readily detectable compositions that are useful for genetic analysis technologies. These compounds and the detectable compositions can aid, for example, in the monitoring of gene expression and the detection and screening of mutations and polymorphisms. Thus, the compounds of the invention are suitable for enzymatic incorporation into nucleic acids. Furthermore, the nucleic acids to which the labeling compound are attached maintain their ability to bind to a probe, such as, for example a complementary nucleic acid.

The present invention provides nucleic acid labeling compounds that are capable of being enzymatically incorporated into a nucleic acid. The nucleic acids to which the compounds are attached maintain their ability to bind to a complementary nucleic acid sequence.

DETAILED DESCRIPTION OF THE INVENTION

Figure 1:
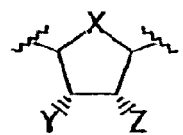
FIG. 1 illustrates a non-limiting set of template moieties.
Figure 1:
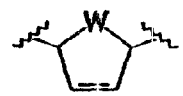
Figure 1:
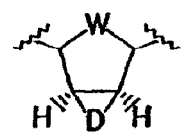
Figure 1:
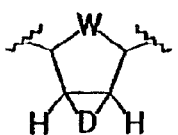
Figure 1:
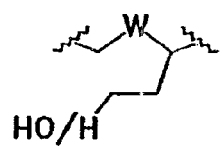
Figure 1:
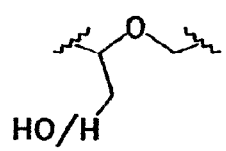
Figure 1:
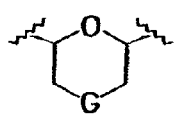
Figure 1:
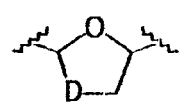
Figure 1:
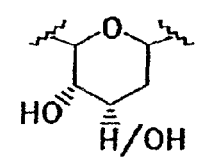
Figure 1:
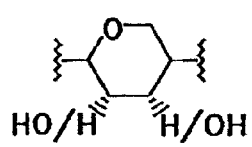
Figure 1:
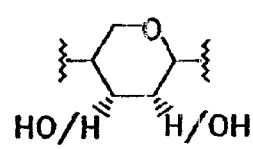
Figure 1:
Figure 1:
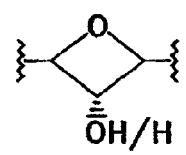
Figure 1:
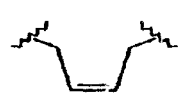
Figure 1:
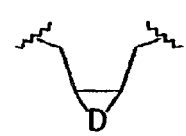

The nucleic acid labeling compounds of the present invention have the following structure:

$$A\text{-}T\text{-}H_c\text{-}L\text{-}(M)_m\text{-}Q, \text{ or } A\text{-}T(H_c)\text{-}L\text{-}(M)_m\text{-}Q, \text{ or } A\text{-}T\text{-}Q$$

wherein A is hydrogen or a functional group that permits the attachment of the nucleic acid labeling compound to a nucleic acid; T is a template moiety; $H_c$ is a heterocyclic group; L is a linker moiety; M is a connecting group; and Q is a detectable moiety.

In one embodiment, the nucleic acid labeling compounds have the following structures:

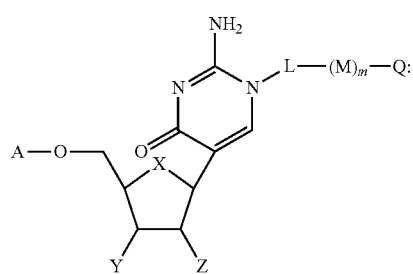

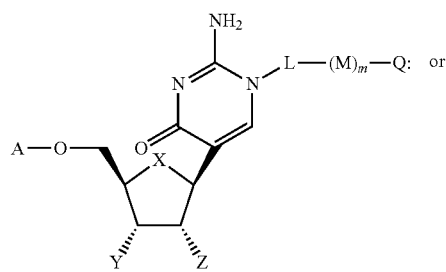

IB

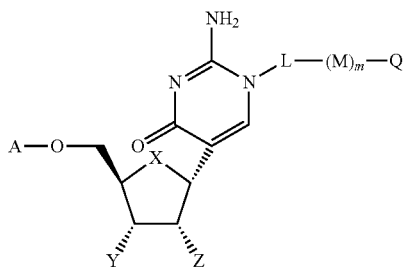

wherein A is hydrogen or a functional group that permits the attachment of the nucleic acid labeling compound to a nucleic acid; X is O, S, $NR_1$ or $CHR_2$, wherein $R_1$ and $R_2$ are, independently, hydrogen, alkyl or aryl; Y is hydrogen, $N_3$, F, $OR_9$, $SR_9$ or $NHR_9$, wherein $R_9$ is hydrogen, alkyl or aryl; Z is hydrogen, $N_3$, F, $OR_9$, $SR_9$ or $NHR_{10}$, wherein $R_{10}$ is hydrogen, alkyl or aryl; L is a linker moiety; Q is a detectable moiety; and M is a connecting group, wherein m is an integer ranging from 0 to about 20.

In another embodiment, A is H or $H_4O_9P_3$—; X is O; Y is H or $OR_9$, wherein $R_9$ is hydrogen, alkyl or aryl; Z is hydrogen, $N_3$, F or $OR_{10}$, wherein $R_{10}$ is hydrogen, alkyl or aryl; and L is amido alkyl and M is -$(M_1)_a$-$(M_2)_b$- wherein a and b are independently integers from 0 to about 5 and the sum of a and b is not greater than 15.

In another embodiment, L is —$(CH_2)_nC(O)NR_3$—, wherein $R_3$ is hydrogen, alkyl or aryl and n is an integer ranging from about 1 to about 10; $M_1$ is —$(CH_2)_iO$— and $M_2$ is —$(CH_2)_jNH$—, wherein i and j are independently integers from 1 to about 5.

In another embodiment, Y is H or OH; Z is H or OH; -L is —$CH_2C(O)NH$—; $M_1$ is —$(CH_2CH_2O)_3$— and $M_2$ is —$CH_2CH_2NH$—; and Q is biotin or a carboxyfluorescein.

In another embodiment, Y is OH; Z is OH; -L-$(M)_m$- is —$CH_2C(O)NH$—$(CH_2CH_2O)_3$—$CH_2CH_2NH$—; and Q is biotin or Y is OH; Z is OH; -L-$(M)_m$- is —$CH_2C(O)NH$—$(CH_2CH_2O)_3$—$CH_2CH_2NH$—; Q is carboxyfluorescein.

In another embodiment, A is H or $H_4O_9P_3$—; X is O; Y is H or $OR_9$, wherein $R_9$ is hydrogen, alkyl or aryl; Z is hydrogen, $N_3$, F or $OR_{10}$, wherein $R_{10}$ is hydrogen, alkyl or aryl; and L is amido alkyl and M is -$(M_1)_a$-$(M_2)_b$-$(M_3)_c$-$(M_4)_d$- wherein a, b, c, and d are independently integers from 0 to about 5 and the sum of a, b, c, and d is not greater than 15.

In another embodiment, L is —$(CH_2)_nC(O)NR_3$—, wherein $R_3$ is hydrogen, alkyl or aryl and n is an integer ranging from about 1 to about 10; each M is independently —$C(O)(CH_2)_kO$—, —$(CH_2)_iO$— or —$(CH_2)_jNH$—, wherein i, j and k are independently integers from 1 to about 5.

In another embodiment, L is —$CH_2C(O)NR_3$—, wherein $R_3$ is hydrogen or, alkyl; $M_1$ is —$(CH_2)_2NH$—, $M_2$ is —$C(O)(CH_2)_2O$—, $M_3$ is —$(CH_2CH_2O)_3$— and $M_4$ is —$(CH_2)_2NH$—.

In another embodiment, Y is OH; Z is OH; -L-$(M)_m$- is —$CH_2C(O)NH$—$CH_2CH_2NH$—$C(O)CH_2CH_2O$—$(CH_2CH_2O)_3$—$CH_2CH_2NH$—; Q is biotin.

In another embodiment, Y is OH; Z is OH; -L-$(M)_m$- is —$CH_2C(O)NH$—$CH_2CH_2NH$—; m is 1; and Q is carboxyfluorescein.

In another embodiment, L is —$(CH_2)_2C(O)NR_3$—, wherein $R_3$ is hydrogen or, alkyl; $M_1$ is —$(CH_2)_2NH$—, $M_2$ is —$C(O)(CH_2)_2O$—, $M_3$ is —$(CH_2CH_2O)_3$— and $M_4$ is —$(CH_2)_2NH$—.

In another embodiment, Y is OH; Z is OH; -L-$(M)_m$- is —$CH_2C(O)NH$—$CH_2CH_2NH$—$C(O)CH_2CH_2O$—$(CH_2CH_2O)_3$—$CH_2CH_2NH$—; Q is biotin.

In another embodiment, Y is OH; Z is OH; -L-$(M)_m$- is —$CH_2CH_2C(O)NH$—$CH_2CH_2NH$—; m is 1; and Q is carboxyfluorescein.

In another embodiment, A is H or $H_4O_9P_3$—; X is O; Y is H or $OR_9$, wherein $R_9$ is hydrogen, alkyl or aryl; Z is hydrogen, $N_3$, F or $OR_{10}$, wherein $R_{10}$ is hydrogen, alkyl or aryl; and L is functionalized alkyl and M is -$(M_1)_a$-$(M_2)_b$-$(M_3)_c$-$(M_2)_d$- wherein a, b, c, and d are independently integers from 0 to about 5 and the sum of a, b, c, and d is not greater than 15.

In another embodiment, L is —$(CH_2)_nO$—, wherein n is an integer ranging from about 1 to about 10; each M is independently —$C(O)(CH_2)_kO$—, —$(CH_2)_i$— or —$(CH_2)_jNH$—, wherein i, j and k are independently integers from 1 to about 5.

In another embodiment, L is —$CH_2O$—; $M_1$ is —$(CH_2)_2NH$—, $M_2$ is —$C(O)(CH_2)_2O$—, $M_3$ is —$(CH_2CH_2O)_3$— and $M_4$ is —$(CH_2)_2NH$—.

In another embodiment, Y is OH; Z is OH; -L-$(M)_m$- is —$CH_2O$—$CH_2CH_2NH$—$C(O)(CH_2)_2O$—$(CH_2CH_2O)_3$—$CH_2CH_2NH$—; Q is biotin or Y is OH; Z is OH; -L-$(M)_m$- is —$CH_2O$—$CH_2CH_2NH$—; m is 1; and Q is carboxyfluorescein.

In another embodiment, L is —$(CH_2)_nNR_3$—, wherein $R_3$ is hydrogen, alkyl or aryl and n is an integer ranging from about 1 to about 10; each M is independently —$C(O)(CH_2)_kO$—, —$(CH_2)_iO$— or —$(CH_2)_jNH$—, wherein i, j and k are independently integers from 1 to about 5.

In another embodiment, L is —$(CH_2)_6$—$NH$—; $M_1$ is —$(CH_2)_2NH$—, $M_2$ is —$C(O)(CH_2)_2O$—, and $M_3$ is —$(CH_2CH_2O)_3$—. In another embodiment, Y is OH; Z is OH; -L-$(M)_m$- is —$(CH_2)_6NH$—$C(O)(CH_2)_2O$—$(CH_2CH_2O)_3$—$CH_2CH_2NH$—; and Q is biotin or Y is OH; Z is OH; L is —$(CH_2)_6NH$—; m is 0; and Q is carboxyfluorescein.

In another embodiment, A is H or $H_4O_9P_3$—; X is O; Y is H or $OR_9$, wherein $R_9$ is hydrogen, alkyl or aryl; Z is hydrogen, $N_3$, F or $OR_{10}$, wherein $R_{10}$ is hydrogen, alkyl or aryl; and L is alkenyl alkyl and M is -$(M_1)_a$-$(M_2)_b$-$(M_3)_c$-$(M_4)_d$- wherein a, b, c, and d are independently integers from 0 to about 5 and the sum of a, b, c, and d is not greater than 15.

In another embodiment, L is -structure —CH=CH—$(CH_2)_nC(O)N(R_6)$—, wherein $R_6$ is hydrogen, alkyl or aryl and n is an integer ranging from about 0 to about 10; each M is independently —$C(O)(CH_2)_kO$—, —$(CH_2)_iO$— or —$(CH_2)_jNH$—, wherein i, j and k are independently integers from 1 to about 5.

In another embodiment, L is —CH=CH—C(O)N(H); $M_1$ is —$(CH_2)_2NH$—, $M_2$ is —$C(O)(CH_2)_2O$—, $M_3$ is —$(CH_2CH_2O)_3$— and $M_4$ is —$(CH_2)_2NH$—.

In another embodiment, Y is OH; Z is OH; -L-$(M)_m$- is —CH=CH—C(O)NH—$CH_2CH_2NH$—$C(O)(CH_2)_2O$—$(CH_2CH_2)_3$—$CH_2CH_2NH$—; Q is biotin or Y is OH; Z is OH; -L-$(M)_m$- is —CH=CH—C(O)NH—$CH_2CH_2NH$—; m is 1; and Q is carboxyfluorescein.

In another embodiment, the nucleic acid labeling compounds have the following structure;

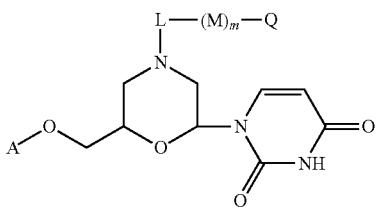

II wherein A is hydrogen or a functional group that permits the attachment of the nucleic acid labeling compound to a nucleic acid; L is a linker moiety; Q is a detectable moiety; and M is a connecting group, wherein m is an integer ranging from 0 to about 3.

In another embodiment, A is H or $H_4O_9P_3$—; L is alkanoyl; and Q is biotin or a carboxyfluorescein; M is —$NR_3$— where $R_3$ is hydrogen or alkyl, and wherein m is 1 or 0.

In another embodiment, L is —$C(O)(CH_2)_n$— wherein n is an integer ranging from about 1 to about 10; M is —NH—; Q is biotin or a carboxyfluorescein.

In another embodiment, -L-$(M)_m$- is —$C(O)(CH_2)_6$—NH—; and Q is biotin or -L-$(M)_m$- is —$C(O)(CH_2)_6$—NH—; and Q is carboxyfluorescein.

In another embodiment, the nucleic acid labeling compounds have the following structures;

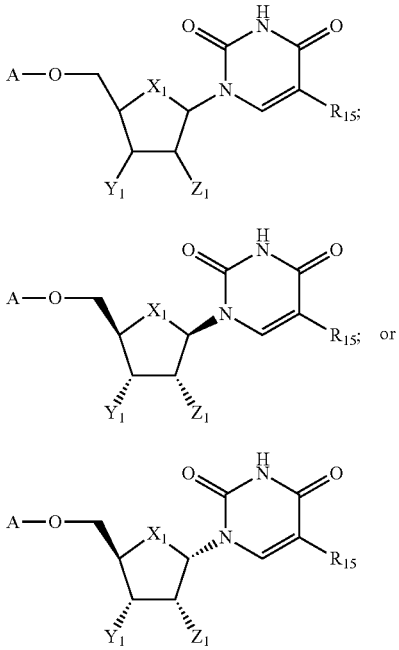

III

IIIB

IIIC wherein A is hydrogen or a functional group that permits the attachment of the nucleic acid labeling compound to a nucleic acid; $X_1$ is O, S, $NR_1$ or $CHR_2$, wherein $R_1$ and $R_2$ are, independently, hydrogen, alkyl or aryl; $R_{15}$ is hydrogen, alkyl or aryl; $Y_1$ is hydrogen, $N_3$, F, $OR_9$, $SR_9$ or $NHR_9$, wherein $R_9$ is hydrogen, alkyl or aryl; $Z_1$ is hydrogen, $N_3$, F, $OR_9$, $SR_9$ or $NHR_{10}$, wherein $R_{10}$ is hydrogen, alkyl or aryl; wherein one of $Y_1$ or $Z_1$ is a group having the formula —$X_2$L-$(M)_m$-Q; $X_2$ is O, S, or $NR_{16}$, and $R_{16}$ is hydrogen, alkyl or aryl; L is a linker moiety; Q is a detectable moiety; and M is a connecting group, wherein m is an integer ranging from 0 to about 20.

In another embodiment, A is H or $H_4O_9P_3$—; $X_1$ is O; $Y_1$ is hydrogen, $OR_9$, wherein $R_9$ is hydrogen, or alkyl, or —$NR_{16}$-$(M)_m$-Q; wherein $R_{16}$ is hydrogen, alkyl or aryl; $Z_1$ is hydrogen $OR_{10}$, wherein $R_{10}$ is hydrogen, or alkyl, or —$NR_{16}$-L-$(M)_m$-Q, wherein $R_{16}$ is hydrogen, or alkyl; L is N-alkyl amido; $R_{15}$ is hydrogen or alkyl; M is —$(CH_2)_nNR_3$— where $R_3$ is hydrogen or alkyl, and m is from 1 to about 15.

In another embodiment, $Y_1$ is hydrogen or OH; $Z_1$ is —NH-L-$(M)_m$-Q; L is —$(CH_2)_n$NHC(O)— where n is an integer from 1 to about 10; M is —$NH(CH_2)_p$— where p is an integer from 1 to about 10; $R_3$ is hydrogen or methyl; and Q is biotin or a carboxyfluorescein.

In another embodiment, $Y_1$ is OH; $R_{15}$ is hydrogen; -L-$(M)_m$- is —$(CH_2)_4$NH—$C(O)(CH_2)_5$NH—; and Q is biotin.

In another embodiment, $Y_1$ is OH; $R_{15}$ is hydrogen; -L-$(M)_m$- is —$(CH_2)_4$NH—$C(O)(CH_2)_5$NH—; and Q is a carboxyfluorescein.

In another embodiment, $Y_1$ is OH; $R_{15}$ is methyl; -L-$(M)_m$- is —$(CH_2)_4$NH—$C(O)(CH_2)_5$NH—; and Q is biotin.

In another embodiment, $Y_1$ is OH; $R_{15}$ is methyl; -L-$(M)_m$- is —$(CH_2)_4$NH—$C(O)(CH_2)_5$NH—; and Q is a carboxyfluorescein.

In another embodiment, $Y_1$ is —NH-L-$(M)_m$-Q; $Z_1$ is hydrogen or OH; L is —$(CH_2)_n$NHC(O)— where n is an integer from 1 to about 10; M is —$NH(CH_2)_p$— where n is an integer from 1 to about 10; $R_{15}$ is hydrogen or methyl; and Q is biotin or a carboxyfluorescein.

In another embodiment, $Z_1$ is OH; $R_{15}$ is hydrogen -L-$(M)_m$- is —$(CH_2)_4$NH—$C(O)(CH_2)_5$NH—; and Q is biotin.

In another embodiment, of the nucleic acid labeling compound, $Z_1$ is OH; $R_{15}$ is hydrogen; -L-$(M)_m$- is —$(CH_2)_4$NH—$C(O)(CH_2)_5$NH—; and Q is a carboxyfluorescein.

In another embodiment, $Z_1$ is OH; $R_{15}$ is methyl; -L-$(M)_m$- is —$(CH_2)_4$NH—$C(O)(CH_2)_5$NH—; and Q is biotin.

In another embodiment, $Z_1$ is OH; $R_{15}$ is methyl; -L-$(M)_m$- is —$(CH_2)_4$NH—$C(O)(CH_2)_5$NH—; and Q is a carboxyfluorescein.

In another embodiment, A is H or $H_4O_9P_3$—; $X_1$ is O; $Y_1$ is hydrogen, $OR_9$, wherein $R_9$ is hydrogen, or alkyl, or —O-L-$(M)_m$-Q; $Z_1$ is hydrogen $OR_{10}$, wherein $R_{10}$ is hydrogen, or alkyl, or —O-L-$(M)_m$-Q, or alkyl; L is alkylene; and m is from 1 to about 10.

In another embodiment, $Y_1$ is hydrogen or OH; $Z_1$ is —O-L-$(M)_m$-Q; L is —$(CH_2)_n$— where n is an integer from 1 to about 12; M is —NH—; $R_{15}$ is hydrogen or methyl; and Q is biotin or a carboxyfluorescein.

In another embodiment, $Y_1$ is OH; $R_{15}$ is hydrogen; -L-$(M)_m$- is —$(CH_2)_6$—NH—; and Q is biotin.

In another embodiment, wherein $Y_1$ is OH; $R_{15}$ is hydrogen; -L-$(M)_m$- is —$(CH_2)_6$—NH—; and Q is a carboxyfluorescein.

In another embodiment, $Y_1$ is OH; $R_{15}$ is methyl; -L-$(M)_m$- is —$(CH_2)_6$—NH—; and Q is biotin.

In another embodiment, $Y_1$ is OH; $R_{15}$ is methyl; -L-$(M)_m$- is —$(CH_2)_6$—NH—; and Q is a carboxyfluorescein.

In another embodiment, $Y_1$ is —O-L-$(M)_m$-Q; $Z_1$ is hydrogen or OH; L is —$(CH_2)_n$— where n is an integer from 1 to about 12; M is —NH—; $R_{15}$ is hydrogen or methyl; and Q is biotin or a carboxyfluorescein.

In another embodiment, $Z_1$ is OH; $R_{15}$ is hydrogen; -L-$(M)_m$- is —$(CH_2)_6$—NH—; and Q is biotin.

In another embodiment, $Z_1$ is OH; $R_{15}$ is hydrogen; -L-$(M)_m$- is —$(CH_2)_6$—NH—; and Q is a carboxyfluorescein.

In another embodiment, $Z_1$ is OH; $R_{15}$ is methyl; -L-$(M)_m$- is —$(CH_2)_6$—NH—; and Q is biotin.

In another embodiment, $Z_1$ is OH; $R_{15}$ is methyl; -L-$(M)_m$- is —$(CH_2)_6$—NH—; and Q is a carboxyfluorescein.

In another embodiment, A is H or $H_4O_9P_3$—; $X_1$ is O; $Y_1$ is hydrogen, $OR_9$, wherein $R_9$ is hydrogen, or alkyl, or —S-L-$(M)_m$-Q; $Z_1$ is hydrogen $OR_{10}$, wherein $R_{10}$ is hydrogen, or alkyl, or —S-L-$(M)_m$-Q; L is alkylene; $X_2$ is S; and m is from 1 to about 10.

In another embodiment, $Y_1$ is hydrogen or OH; $Z_1$ is —S-L-$(M)_m$-Q; L is —S—$(CH_2)_n$— where n is an integer from 1 to about 10; M is —NH—; $R_{15}$ is hydrogen or methyl; and Q is biotin or a carboxyfluorescein.

In another embodiment, $Y_1$ is OH; $R_{15}$ is hydrogen; -L-$(M)_m$- is —S—$(CH_2)_n$—NH—; and Q is biotin.

In another embodiment, $Y_1$ is OH; $R_{15}$ is hydrogen; -L-$(M)_m$- is —S—$(CH_2)_2$—NH—; and Q is a carboxyfluorescein.

In another embodiment, $Y_1$ is OH; $R_{15}$ is methyl; -L-$(M)_m$- is —S—$(CH_2)_2$—NH—; and Q is biotin.

In another embodiment, $Y_1$ is OH; $R_{15}$ is methyl; -L-$(M)_m$- is —S—$(CH_2)_2$—NH—; and Q is a carboxyfluorescein.

In another embodiment, $Y_1$ is —S-L-$(M)_m$-Q; $Z_1$ is hydrogen or OH; L is —S—$(CH_2)_n$— where n is an integer from 1 to about 10; M is —NH—; $R_{15}$ is hydrogen or methyl; and Q is biotin or a carboxyfluorescein.

In another embodiment, —$Z_1$ is OH; $R_{15}$ is hydrogen; -L-$(M)_m$- is —S—$(CH_2)_2$—NH—; and Q is biotin.

In another embodiment, $Z_1$ is OH; $R_{15}$ is hydrogen; -L-$(M)_m$- is —S—$(CH_2)_2$—NH—; and Q is a carboxyfluorescein.

In another embodiment, $Z_1$ is OH; $R_{15}$ is methyl; -L-$(M)_m$- is —S—$(CH_2)_2$—NH—; and Q is biotin.

In another embodiment, $Z_1$ is OH; $R_{15}$ is methyl; -L-$(M)_m$- is —S—$(CH_2)_2$—NH—; and Q is a carboxyfluorescein.

In another embodiment, the nucleic acid labeling compounds have the following structure:

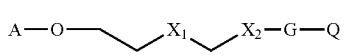

IV wherein A is hydrogen or a functional group that permits the attachment of the nucleic acid labeling compound to a nucleic acid; $X_1$ is O, S, $NR_1$ or $CHR_2$, wherein $R_1$ and $R_2$ are, independently, hydrogen, alkyl or aryl; $X_2$ is a bond or alkylene; Q is a detectable moiety; and G is -L-$(M)_m$- where L is a linker moiety and each M a connecting group, where m is from 0 to about 20.

In another embodiment, A is H or $H_4O_9P_3$—; $X_1$ is O; $X_2$ is a bond; and G is —C(O)$NR_3$—$(CH_2)_m$—$(CH_2CH_2O)_n$—$CH_2CH_2$—C(O)$NR_3$—, where $R_3$ is hydrogen or alkyl, and m and n are independently an integer from 1 to about 15.

In another embodiment, G is

—C(O)NH—$(CH_2)_m$—$(CH_2CH_2O)_n$—$CH_2CH_2$—C(O)NH— where m is from 1 to about 6 and n is from 1 to about 4. Preferably, n is 3 or 4 and m is 5 or 6.

In another embodiment, A is H or $H_4O_9P_3$—; $X_1$ is O; $X_2$ is $CH_2$; and G is —C(O)$NR_3$—$(CH_2)_m$—$(CH_2CH_2O)_n$—$CH_2CH_2$—C(O)$NR_3$—, where $R_3$ is hydrogen or alkyl, and m and n are independently an integer from 1 to about 15.

In another embodiment, A is H or $H_4O_9P_3$—; $X_1$ is O; $X_2$ is $CH_2$; and G is —C(O)$NR_3$—$(CH_2)_m$—$(CH_2CH_2O)_n$—$CH_2CH_2$—C(O)$NR_3$—, where $R_3$ is hydrogen or alkyl, and m and n are independently an integer from 1 to about 15.

The present invention also provides nucleic acid derivatives produced by coupling a nucleic acid labeling compound with a nucleic acid and hybridization products comprising the nucleic acid derivatives bound to a complementary probe.

The present invention also provides nucleic acid derivatives produced by coupling one of the nucleic acid labeling compounds of the invention with a nucleic acid and the hybridization products comprising the nucleic acid derivatives bound to a complementary probe. The hybridization product formed from the nucleic acid derivatives comprise the nucleic acid derivative bound to a complementary probe. In one embodiment, the probe is attached to a glass chip.

The present invention also provides methods of synthesizing nucleic acid derivatives by attaching a nucleic acid labeling compound to a nucleic acid. It further provides methods of detecting nucleic acids involving incubating the nucleic acid derivatives with a probe.

In yet another embodiment, the methods involve the steps of: (a) providing at least one nucleic acid coupled to a support; (b) providing a labeled moiety capable of being coupled with a terminal transferase to said nucleic acid; (c) providing said terminal transferase; and (d) coupling said labeled moiety to said nucleic acid using said terminal transferase.

In still another embodiment, the methods involve the steps of: (a) providing at least two nucleic acids coupled to a support; (b) increasing the number of monomer units of said nucleic acids to form a common nucleic acid tail on said at least two nucleic acids; (c) providing a labeled moiety capable of recognizing said common nucleic acid tails; and (d) contacting said common nucleic acid tails and said labeled moiety.

In still yet another embodiment, the methods involve the steps of: (a) providing at least one nucleic acid coupled to a support; (b) providing a labeled moiety capable of being coupled with a ligase to said nucleic acid; (c) providing said ligase; and (d) coupling said labeled moiety to said nucleic acid using said ligase.

This invention also provides compounds of the formulas described herein.

Definitions

The following definitions are used, unless otherwise described. Halo is fluoro, chloro, bromo, or iodo. Alkyl, alkoxy, aralkyl, alkylaryl, etc, denote both straight and branched alkyl groups; but reference to an individual radical such as "propyl" embraces only the straight chain radical, a branched chain isomer such as "isopropyl" being specifically referred to. Aryl includes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$-$C_4$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

"Alkyl" refers to a straight chain, branched or cyclic chemical groups containing only carbon and hydrogen. Alkyl groups include, without limitation, ethyl, propyl, butyl, pentyl, cyclopentyl and 2-methylbutyl. Alkyl groups are unsubstituted or substituted with 1 or more substituents (e.g., halogen, alkoxy, amino).

"Alkylene" refers to a straight chain, branched or cyclic chemical group containing only carbon and hydrogen. Alkyl groups include, without limitation, ethylene, propylene, butylene, pentylene, and 2-methylbutylene. Alkyl groups are unsubstituted or substituted with 1 or more substituents (e.g., halogen, alkoxy, amino).

"Aryl" refers to a monovalent, unsaturated aromatic carbocyclic group. Aryl groups include, without limitation, phenyl, naphthyl, anthryl and biphenyl. Aryl groups are unsubstituted or substituted with 1 or more substituents (e.g., halogen, alkoxy, amino). "Arylene" refers to a divalent aryl group.

"Amido" refers to a chemical group having the structure —C(O)NR$_3$—, wherein R$_3$ is hydrogen, alkyl or aryl. Preferably, the amido group is of the structure —C(O)NR$_3$— where R3 is hydrogen or alkyl having from about 1 to about 6 carbon atoms. More preferably, the amido alkyl group is of the structure —C(O)NH—.

"Alkanoyl" refers to a chemical group having the structure —(CH$_2$)$_n$C(O)—, n is an integer ranging from 0 to about 10. Preferably, the alkanoyl group is of the structure —(CH$_2$)$_n$C(O)—, wherein n is an integer ranging from about 2 to about 10. More preferably, the alkanoyl group is of the structure —(CH$_2$)$_n$C(O)—, wherein n is an integer ranging from about 2 to about 6. Most preferably, the alkanoyl group is of the structure —CH$_2$C(O)—.

"Alkyl amido" refers to a chemical group having the structure —R$_4$C(O)NR$_3$—, wherein R$_3$ is hydrogen, alkyl or aryl, and R$_4$ is alkylene or arylene. Preferably, the alkyl amido group is of the structure —(CH$_2$)$_n$C(O)NH—, wherein n is an integer ranging from about 1 to about 10. More preferably, n is an integer ranging from about 1 to about 6. Most preferably, the alkyl amido group has the structure —(CH$_2$)$_2$C(O)NH— or the structure —CH$_2$C(O)NH—.

"N-Amido alkyl" refers to a chemical group having the structure —C(O)NR$_3$R$_4$—, wherein R$_3$ is hydrogen, alkyl or aryl, and R$_4$ is alkylene or arylene. Preferably, the N-amido alkyl group is of the structure —C(O)NH(CH$_2$)$_n$R$_5$—, wherein n is an integer ranging from about 2 to about 10, and R$_5$ is O, NR$_6$, or C(O), and wherein R$_6$ is hydrogen, alkyl or aryl. More preferably, the N-amido alkyl group is of the structure —C(O)NH(CH$_2$)$_n$N(H)—, wherein n is an integer ranging from about 2 to about 6. Most preferably, the N-amido alkyl group is of the structure —C(O)NH(CH$_2$)$_4$N(H)—.

"Alkynyl alkyl" refers to a chemical group having the structure —C≡C—R$_4$—, wherein R$_4$ is alkyl or aryl. Preferably, the alkynyl alkyl group is of the structure —C≡C—(CH$_2$)$_n$R$_5$—, wherein n is an integer ranging from 1 to about 10, and R$_5$ is O, NR$_6$ or C(O), wherein R$_6$ is hydrogen, alkyl or aryl. More preferably, the alkynyl alkyl group is of the structure —C≡C—(CH$_2$)$_n$N(H)—, wherein n is an integer ranging from 1 to about 4. Most preferably, the alkynyl alkyl group is of the structure —C≡C—CH$_2$N(H)—.

"Alkenyl alkyl" refers to a chemical group having the structure —CH=CH—R$_4$—, wherein R$_4$ is a bond, alkyl or aryl. Preferably, the alkenyl alkyl group is of the structure —CH=CH—(CH$_2$)$_n$R$_5$—, wherein n is an integer ranging from 0 to about 10, and R$_5$ is O, NR$_6$, C(O) or C(O)NR$_6$, wherein R$_6$ is hydrogen, alkyl or aryl. More preferably, the alkenyl alkyl group is of the structure —CH=CH—(CH$_2$)$_n$C(O)NR$_6$—, wherein n is an integer ranging from 0 to about 4. Most preferably, the alkenyl alkyl group is of the structure —CH=CH—C(O)N(H)—.

"Functionalized alkyl" refers to a chemical group of the structure —(CH$_2$)$_n$R$_7$—, wherein n is an integer ranging from 1 to about 10, and R$_7$ is O, S, NH or C(O). Preferably, the functionalized alkyl group is of the structure —(CH$_2$)$_n$C(O)—, wherein n is an integer ranging from 1 to about 4. More preferably, the functionalized alkyl group is of the structure —CH$_2$C(O)—.

"Alkoxy" refers to a chemical group of the structure —O(CH$_2$)$_n$R$_8$—, wherein n is an integer ranging from 2 to about 10, and R$_8$ is a bond, O, S, NH or C(O). Preferably, the alkoxy group is of the structure —O(CH$_2$)$_n$—, wherein n is an integer ranging from 2 to about 4. More preferably, the alkoxy group is of the structure —OCH$_2$CH$_2$—.

"Alkyl thio" refers to a chemical group of the structure —S(CH$_2$)$_n$R$_8$—, wherein n is an integer ranging from 1 to about 10, and R$_8$ is a bond, O, S, NH or C(O). Preferably, the alkyl thio group is of the structure —S(CH$_2$)$_n$—, wherein n is an integer ranging from 2 to about 4. More preferably, the thio group is of the structure —SCH$_2$CH$_2$C(O)—.

"Amino alkyl" refers to a chemical group having an amino group attached to an alkyl group. Preferably an amino alkyl is of the structure —(CH$_2$)$_n$NH—, wherein n is an integer ranging from about 2 to about 10. More preferably it is of the structure —(CH$_2$)$_n$NH—, wherein n is an integer ranging from about 2 to about 4. Most preferably, the amino alkyl group is of the structure —(CH$_2$)$_2$NH—.

"Nucleic acid" refers to a polymer comprising 2 or more nucleotides and includes single-, double- and triple stranded polymers. "Nucleotide" refers to both naturally occurring and non-naturally occurring compounds and comprises a heterocyclic base, a sugar, and a linking group, preferably a phosphate ester. For example, structural groups may be added to the ribosyl or deoxyribosyl unit of the nucleotide, such as a methyl or allyl group at the 2'-O position or a fluoro group that substitutes for the 2'-O group. The linking group, such as a phosphodiester, of the nucleic acid may be substituted or modified, for example with methyl phosphonates or O-methyl phosphates. Bases and sugars can also be modified, as is known in the art. "Nucleic acid," for the purposes of this disclosure, also includes "peptide nucleic acids" in which native or modified nucleic acid bases are attached to a polyamide backbone.

The phrase "coupled to a support" means bound directly or indirectly thereto including attachment by covalent binding, hydrogen bonding, ionic interaction, hydrophobic interaction, or otherwise.

"Probe" refers to a nucleic acid that can be used to detect, by hybridization, a target nucleic acid. Preferably, the probe is complementary to the target nucleic acid along the entire length of the probe, but hybridization can occur in the presence of one or more base mismatches between probe and target.

"Perfect match probe" refers to a probe that has a sequence that is perfectly complementary to a particular target sequence. The test probe is typically perfectly complementary to a portion (subsequence) of the target sequence. The perfect match (PM) probe can be a "test probe", a "normalization control" probe, an expression level control probe and the like. A perfect match control or perfect match probe is, however, distinguished from a "mismatch control" or "mismatch probe." In the case of expression monitoring arrays, perfect match probes are typically preselected (designed) to be complementary to particular sequences or subsequences of target nucleic acids (e.g., particular genes). In contrast, in generic difference screening arrays, the particular target sequences are typically unknown. In the latter case, prefect match probes cannot be preselected. The term perfect match probe in this context is to distinguish that probe from a corresponding "mismatch control" that differs from the perfect match in one or more particular preselected nucleotides as described below.

"Mismatch control" or "mismatch probe", in expression monitoring arrays, refers to probes whose sequence is deliberately selected not to be perfectly complementary to a particular target sequence. For each mismatch (MM) control in a high-density array there preferably exists a corresponding perfect match (PM) probe that is perfectly complementary to the same particular target sequence. In "generic" (e.g., random, arbitrary, haphazard, etc.) arrays, since the target nucleic acid(s) are unknown perfect match and mismatch probes cannot be a priori determined, designed, or selected. In this instance, the probes are preferably provided as pairs where each pair of probes differ in one or more preselected nucleotides. Thus, while it is not known a priori which of the probes in the pair is the perfect match, it is known that when one probe specifically hybridizes to a particular target sequence, the other probe of the pair will act as a mismatch control for that target sequence. It will be appreciated that the perfect match and mismatch probes need not be provided as pairs, but may be provided as larger collections (e.g., 3, 4, 5, or more) of probes that differ from each other in particular preselected nucleotides. While the mismatch(es) may be located anywhere in the mismatch probe, terminal mismatches are less desirable as a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions. In a particularly preferred embodiment, perfect matches differ from mismatch controls in a single centrally-located nucleotide.

"Labeled moiety" refers to a moiety capable of being detected by the various methods discussed herein or known in the art.

Nucleic Acid Labeling Compounds

The nucleic acid labeling compounds of the present invention are of the following structure;

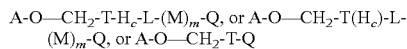

wherein A is hydrogen or a functional group that permits the attachment of the nucleic acid labeling compound to a nucleic acid; T is an optional template moiety; $H_c$ is an heterocyclic group; L is a linker moiety; Q is a detectable moiety; and M is an connecting group, wherein m is an integer ranging from 0 to about 20. In a preferred embodiment m is from 0 to about 15. In a more preferred embodiment m is from 0 to about 10. In the most preferred embodiment m is from 0 to about 5.

The group A is either hydrogen or a functional group that permits the attachment of a nucleic acid labeling compound to a nucleic acid. Nonlimiting examples of such groups include the following; monophosphate; diphosphate; triphosphate ($H_4O_9P$); phosphoramidite (($R_2N$)(R'O)P), wherein R is linear, branched or cyclic alkyl, and R' is a protecting group such as 2-cyanoethyl; and H-phosphonate (HP(O)O—HNR$_3$), wherein R is linear, branched or cyclic alkyl.

The template moiety (T) is covalently attached to a methylene group (CH$_2$) at one position and a heterocyclic group (H$_c$) or the linker moiety at another position. A nonlimiting set of template moieties is shown in FIG. 1, wherein the substituents are defined as follows; X is O, S, NR$_1$ or CHR$_2$; Y is H, N$_3$, F, OR$_9$, SR$_9$ or NHR$_9$; Z is H, N$_3$, F or OR$_{10}$; W is O, S or CH$_2$; D is O or S; and, G is O, NH or CH$_2$. The substituents R$_1$, R$_2$, R$_9$ and R$_{10}$ are independent of one another and are H, alkyl or aryl.

The heterocyclic group (H$_c$) is a cyclic moiety containing both carbon and a heteroatom.

The linker moiety (L) of the nucleic acid labeling compound is covalently bound to the heterocycle (H$_c$) or the template moiety at one terminal position. It is attached to the detectable moiety (Q) at another terminal position, either directly or through a connecting group (M). It is of a structure that is sterically and electronically suitable for incorporation into a nucleic acid. Nonlimiting examples of linker moieties include amido alkyl groups, functionalized alkyl groups, alkenyl alkyl groups, alkanoyl groups, and N-alkyl amido groups.

Amido groups have the structure —C(O)NR$_3$—, wherein R$_3$ is hydrogen, alkyl or aryl. Preferably, the amido group is of the structure —C(O)NR$_3$— where R$_3$ is hydrogen or alkyl having from about 1 to about 6 carbon atoms. More preferably, the amido alkyl group is of the structure —C(O)NH—.

Alkanoyl groups have the structure —(CH$_2$)$_n$C(O)—, n is an integer ranging from 0 to about 10. Preferably, the alkanoyl group is of the structure —(CH$_2$)$_n$C(O)—, wherein n is an integer ranging from about 2 to about 10. More preferably, the alkanoyl group is of the structure —(CH$_2$)$_n$C(O)—, wherein n is an integer ranging from about 2 to about 6. Most preferably, the alkanoyl group is of the structure —CH$_2$C(O)—.

Amido alkyl groups have the structure —R$_4$C(O)NR$_3$—, wherein R$_3$ is hydrogen, alkyl or aryl, and R$_4$ is alkyl or aryl. The amido alkyl group is preferably of the structure —(CH$_2$)$_n$C(O)NH—, wherein n is an integer ranging from about 1 to about 10. More preferably, n is an integer ranging from about 1 to about 6. Most preferably, the alkyl amido group has the structure —(CH$_2$)$_2$C(O)NH— or the structure —CH$_2$C(O)NH—.

N-Amido alkyl groups have the structure —C(O)NR$_3$R$_4$—, wherein R$_3$ is hydrogen, alkyl or aryl, and R$_4$ is alkylene or arylene. Preferably, the N-amido alkyl group is of the structure —C(O)NH(CH$_2$)$_n$R$_5$—, wherein n is an integer ranging from about 2 to about 10, and R$_5$ is O, NR$_6$, or C(O), and wherein R$_6$ is hydrogen, alkyl or aryl. More preferably, the N-amido alkyl group is of the structure —C(O)NH(CH$_2$)$_n$N(H)—, wherein n is an integer ranging from about 2 to about 6. Most preferably, the N-amido alkyl group is of the structure —C(O)NH(CH$_2$)$_4$N(H)—.

Alkenyl alkyl groups are of the structure —CH═CH—R$_4$—, wherein R$_4$ is alkyl or aryl. The alkenyl alkyl group is preferably of the structure —CH═CH(CH$_2$)$_n$R$_5$—, wherein n is an integer ranging from 1 to about 10, and R$_5$ is O, NR$_6$, C(O) or C(O)NR$_6$, wherein R$_6$ is hydrogen, alkyl or aryl. More preferably, the alkenyl alkyl group is of the structure —CH═CH—(CH$_2$)$_n$C(O)NR$_6$—, wherein n is an integer ranging from 0 to about 4. Most preferably, the alkenyl alkyl group is of the structure —CH═CH—C(O)N(H)—.

Functionalized alkyl groups are of the structure —(CH$_2$)$_n$R$_7$—, wherein n is an integer ranging from 1 to about 10, and R$_7$ is O, S, NH, or C(O). The functionalized alkyl group is preferably of the structure —(CH$_2$)$_n$C(O)—, wherein n is an integer ranging from 1 to about 4. More preferably, the functionalized alkyl group is —CH$_2$C(O)—.

Alkoxy groups are of the structure —O(CH$_2$)$_n$R$_8$—, wherein n is an integer ranging from 2 to about 10, and R$_8$ is O, S, NH, or C(O). The alkoxy group is preferably of the structure —O(CH$_2$)$_n$— or —O(CH$_2$)$_n$C(O)—, wherein n is an integer ranging from 2 to about 4. More preferably, the alkoxy group is of the structure —OCH$_2$CH$_2$— or —OCH$_2$CH$_2$C(O)—.

Alkyl thio groups are of the structure —S(CH$_2$)$_n$R$_8$—, wherein n is an integer ranging from 2 to about 10, and R$_8$ is O, S, NH, or C(O). The alkyl thio group is preferably of the structure —S(CH$_2$)$_n$C(O)—, wherein n is an integer ranging from 2 to about 4. More preferably, the alkyl thio group is of the structure —SCH$_2$CH$_2$C(O)—.

Amino alkyl groups comprise an amino group attached to an alkyl group. Preferably, amino alkyl groups are of the structure —NH(CH$_2$)$_n$NH—, wherein n is an integer ranging from about 2 to about 10. The amino alkyl group is more preferably of the structure —(CH$_2$)$_n$NH—, wherein n is an integer ranging from about 2 to about 4. Most preferably, the amino alkyl group is of the structure —(CH$_2$)$_4$NH—.

The detectable moiety (Q) is a chemical group that provides an signal. The signal is detectable by any suitable means, including spectroscopic, photochemical, biochemical, immunochemical, electrical, optical or chemical means. In certain cases, the signal is detectable by 2 or more means.

The detectable moiety provides the signal either directly or indirectly. A direct signal is produced where the labeling group spontaneously emits a signal, or generates a signal upon the introduction of a suitable stimulus. Radiolabels, such as $^3$H, $^{125}$I, $^{35}$S, $^{14}$C or $^{32}$P, and magnetic particles, such as Dynabeads™, are nonlimiting examples of groups that directly and spontaneously provide a signal. Labeling groups that directly provide a signal in the presence of a stimulus include the following nonlimiting examples; colloidal gold (40-80 nm diameter), which scatters green light with high efficiency; fluorescent labels, such as fluorescein, texas red, rhodamine, and green fluorescent protein (Molecular Probes, Eugene, Oreg.), which absorb and subsequently emit light; chemiluminescent or bioluminescent labels, such as luminol, lophine, acridine salts and luciferins, which are electronically excited as the result of a chemical or biological reaction and subsequently emit light; spin labels, such as vanadium, copper, iron, manganese and nitroxide free radicals, which are detected by electron spin resonance (ESR) spectroscopy; dyes, such as quinoline dyes, triarylmethane dyes and acridine dyes, which absorb specific wavelengths of light; and colored glass or plastic (e.g., polystyrene, polypropylene, latex, etc.) beads. See U.S. Pat. Nos. 3,817,837; 3,850,752; 3,939,350; 3,996,345; 4,277,437; 4,275,149 and 4,366,241.

A detectable moiety provides an indirect signal where it interacts with a second compound that spontaneously emits a signal, or generates a signal upon the introduction of a suitable stimulus. Biotin, for example, produces a signal by forming a conjugate with streptavidin, which is then detected. See Hybridization With Nucleic Acid Probes. In *Laboratory Techniques in Biochemistry and Molecular Biology*, Tijssen, P., Ed.; Elsevier; New York, 1993; Vol. 24. An enzyme, such as horseradish peroxidase or alkaline phosphatase, that is attached to an antibody in a label-antibody-antibody as in an ELISA assay, also produces an indirect signal.

A preferred detectable moiety is a fluorescent group. Fluorescent groups typically produce a high signal to noise ratio, thereby providing increased resolution and sensitivity in a detection procedure. Preferably, the fluorescent group absorbs light with a wavelength above about 300 nm, more preferably above about 350 nm, and most preferably above about 400 nm. The wavelength of the light emitted by the fluorescent group is preferably above about 310 nm, more preferably above about 360 nm, and most preferably above about 410 nm.

The fluorescent detectable moiety is selected from a variety of structural classes, including the following nonlimiting examples; 1- and 2-aminonaphthalene, p,p'diaminostilbenes, pyrenes, quaternary phenanthridine salts, 9-aminoacridines, p,p'-diaminobenzophenone imines, anthracenes, oxacarbocyanine, marocyanine, 3-aminoequilenin, perylene, bisbenzoxazole, bis-p-oxazolyl benzene, 1,2-benzophenazin, retinol, bis-3-aminopridinium salts, hellebrigenin, tetracycline, sterophenol, benzimidazolyl phenylamine, 2-oxo-3-chromen, indole, xanthen, 7-hydroxycoumarin, phenoxazine, salicylate, strophanthidin, porphyrins, triarylmethanes, flavin, xanthene dyes (e.g., fluorescein and rhodamine dyes); cyanine dyes; 4,4-difluoro-4-bora-3a,4a-diaza-s-indacene dyes and fluorescent proteins (e.g., green fluorescent protein, phycobiliprotein).

A number of fluorescent compounds are suitable for incorporation into the present invention. Nonlimiting examples of such compounds include the following; dansyl chloride; fluoresceins, such as 3,6-dihydroxy-9-phenylxanthhydrol; rhodamineisothiocyanate; N-phenyl-1-amino-sulfonatonaphthalene; N-phenyl-2-amino-6-sulfonatonaphthanlene; 4-acetamido-4-isothiocyanatostilbene-2,2'-disulfonic acid; pyrene-3-sulfonic acid; 2-toluidinonapththalene-6-sulfonate; N-phenyl, N-methyl 2-aminonaphthalene-6-sulfonate; ethidium bromide; stebrine; auromine-0,2-(9'-anthroyl)palmitate; dansyl phosphatidylethanolamin; N,N'-dioctadecyl oxacarbocycanine; N,N'-dihexyl oxacarbocyanine; merocyanine, 4-(3'-pyrenyl)butryate; d-3-aminodesoxy-equilenin; 12-(9'-anthroyl)stearate; 2-methylanthracene; 9-vinylanthracene; 2,2'-(vinylene-p-phenylene) bisbenzoxazole; p-bis[2-(4-methyl-5-phenyl oxazolyl)] benzene; 6-dimethylamino-1,2-benzophenzin; retinol; bis (3'-aminopyridinium)-1,10-decandiyl diiodide; sulfonaphthylhydrazone of hellibrienin; chlorotetracycline; N-(7-dimethylamino-4-methyl-2-oxo-3-chromenyl)maleimide; N-[p-(2-benzimidazolyl)phenyl]maleimide; N-(4-fluoranthyl)maleimide; bis(homovanillic acid); resazarin; 4-chloro-7-nitro-2,1,3-benzooxadizole; merocyanine 540; resorufin; rose bengal and 2,4-diphenyl-3(2H)-furanone. Preferably, the fluorescent detectable moiety is a fluorescein or rhodamine dye.

Another preferred detectable moiety is colloidal gold. The colloidal gold particle is typically 40 to 80 nm in diameter. The colloidal gold may be attached to a labeling compound in a variety of ways. In one embodiment, the linker moiety of the nucleic acid labeling compound terminates in a thiol group (—SH), and the thiol group is directly bound to colloidal gold through a dative bond. See Mirkin et al. *Nature* 1996, 382, 607-609. In another embodiment, it is attached indirectly, for instance through the interaction between colloidal gold conjugates of antibiotin and a biotinylated labeling compound. The detection of the gold labeled compound may be enhanced through the use of a silver enhancement method. See Danscher et al. *J. Histotech* 1993, 16, 201-207.

The connecting groups (M)$_m$ may serve to covalently attach the linker group (L) to the detectable moiety (Q). Each M group can be the same or different and can independently be any suitable structure that will not interfere with the function of the labeling compound. Nonlimiting examples of M groups include the following; amino alkyl, —CO(CH$_2$)$_5$NH—, —CO—, —NH—, —CO(O)—, —CO(NH)—, —(CH$_2$)$_i$O—, —(CH$_2$)$_j$NH—, —C(O)(CH$_2$)$_h$O—, —CO(CH$_2$)$_5$NHCO(CH$_2$)$_5$NH—, —NH(CH$_2$CH$_2$O)$_k$NH—, and —CO(CH$_2$)$_5$—; wherein, k is an integer from 1 to about 5, preferably k is 1 or 2; m is an integer ranging from 0 to about 5, preferably 0 to about 3; h, i and j are independently integers from 1 to about 5, preferably 1 to about 3.

Synthesis of Nucleic Acid Labeling Compounds

Figure 2:
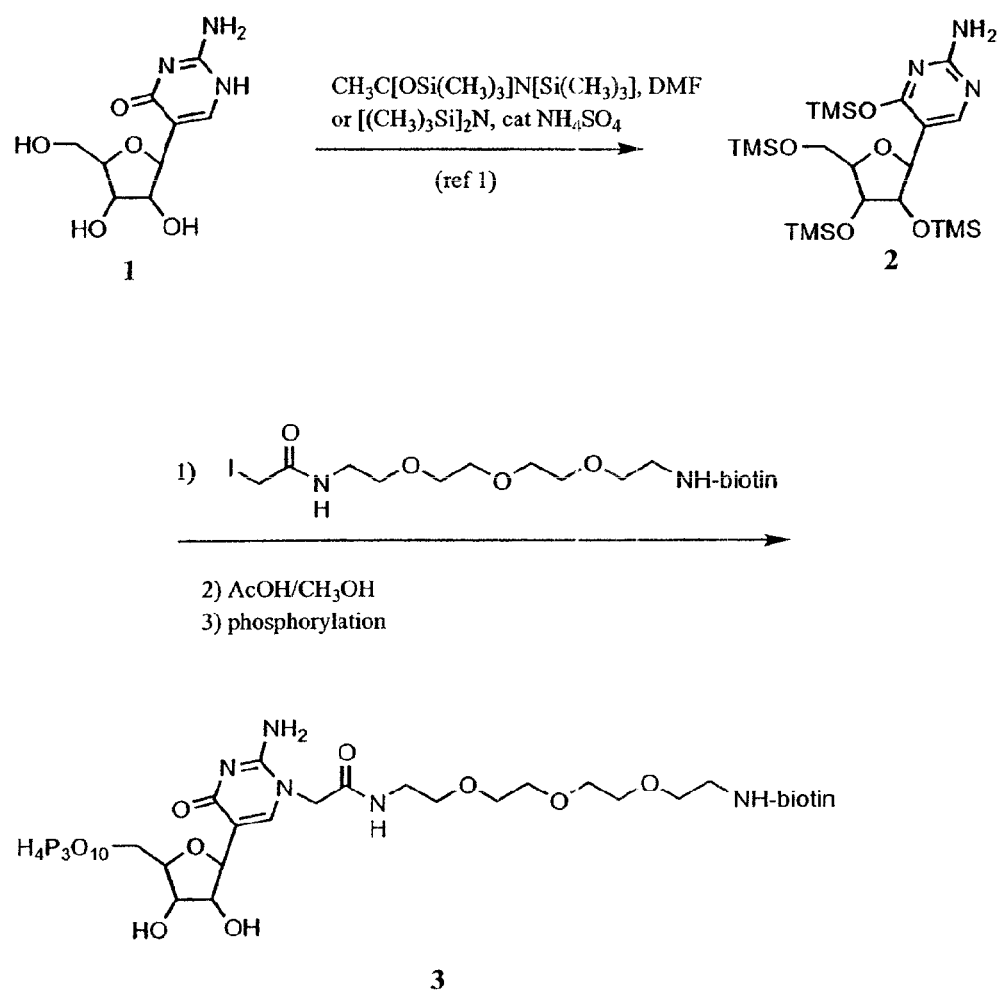
FIGS. 2, 3, 3a, 4, 5, 6, 7, 8, 9, and 10 illustrate synthetic routes to fluorescein and biotin labeled compounds of the invention.

FIG. 2 illustrates a synthetic route to nucleic acid labeling compound, 4, starting from 2-amino-5-(β-D-ribofuranosyl)-4(1H)-pyrimidinone, 1. The hydroxy groups are protected as the trimethyl silylethers according to the procedure described in *J. Antibiot.* 1977, 30, 129. The N1 nitrogen atom is alkylated using a substituted iodoamide having a biotin label attached, according to the procedure described in *Tetrahedron* 1984, 40, 33. (PEO-iodoacetyl biotin can be purchased from Pierce Chemical Co.) The silyl protecting groups are removed, providing a compound having free alcohol groups using acetic acid in methanol. The product is converted into a 5'-triphosphate to afford labeled compound 4.

Figure 3:
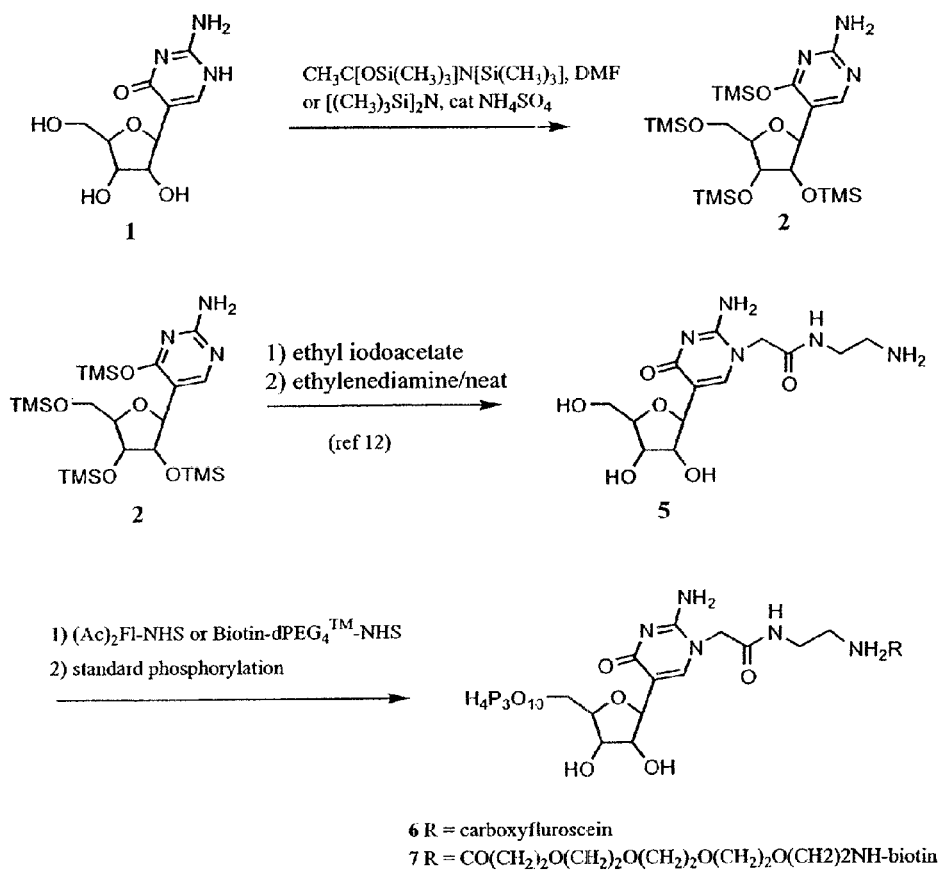

FIG. 3 illustrates a synthetic route to nucleic acid labeling compounds, 6 and 7, starting from 2-amino-5-(β-D-ribofuranosyl)-4(1H)-pyrimidinone, 1. The hydroxy groups are protected as the trimethyl silylethers according to the procedure described in *J. Antibiot.* 1977, 30, 129. The N1 nitrogen atom is alkylated according to the procedure described in *Tetrahedron* 1984, 40, 33, using ethyl iodoacetate. The ester is converted to amide, 5, using ethylene diamine. The biotin labeled compound is prepared by reacting amide, 5, with biotin-dPEG4™-NHS (purchased from Quanta Biodesign). Alternatively, amide 5 is reacted with 5-carboxyfluorescein-NHS. The silyl protecting groups are removed to provide a compound having free alcohol groups, using acetic acid in methanol. The product is converted into a 5'-triphosphate using standard phosphorylation conditions to afford, respectively, nucleic acid labeling compounds 6 and 7.

Figure 4:
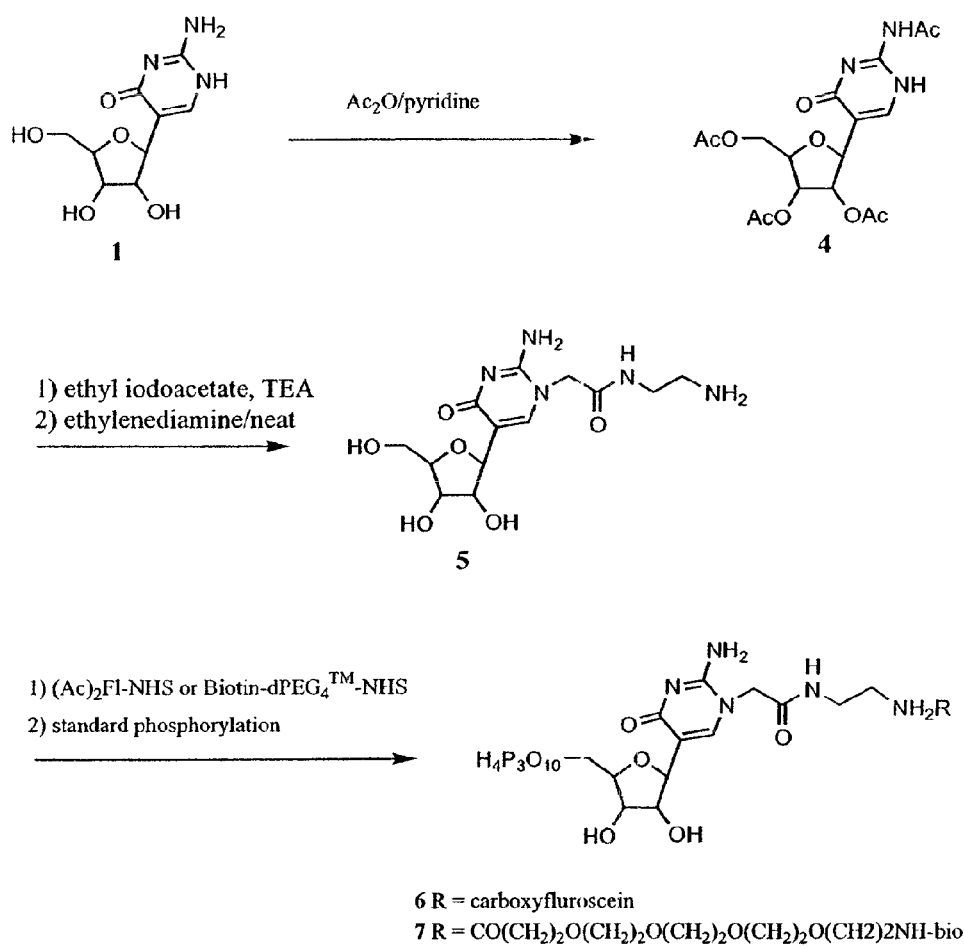

FIG. 4 illustrates an alternate synthetic route to nucleic acid labeling compounds, 6 and 7, starting from 2-amino-5-(β-D-ribofuranosyl)-4(1H)-pyrimidinone, 1. The hydroxy groups are protected as acetyl esters using acetic anhydride in pyridine. The N1 nitrogen atom is alkylated according to the procedure described in *Tetrahedron* 1984, 40, 33, using ethyl iodoacetate. The ester is converted to amide, 8, using ethylene diamine. The biotin labeled compound is prepared by reacting amide, 8, with biotin-dPEG4™-NHS (purchased from Quanta Biodesign). Alternatively, amide 8 is reacted with 5-carboxyfluorescein-NHS. The silyl protecting groups are removed to provide a compound having free alcohol groups, using acetic acid in methanol. The product is converted into a 5'-triphosphate using standard phosphorylation conditions to afford, respectively, nucleic acid labeling compounds 6 and 7.

Figure 5:
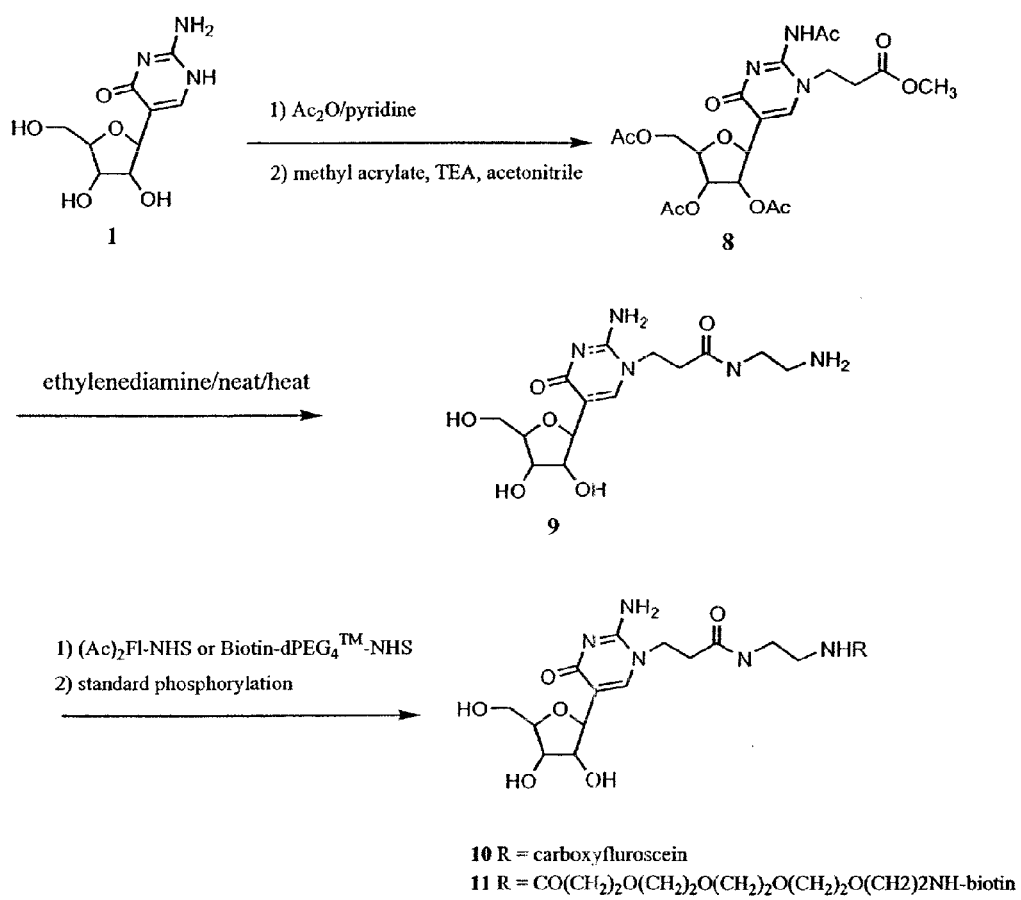

FIG. 5 illustrates a synthetic route to nucleic acid labeling compounds, 10 and 11, starting from 2-amino-5-(β-D-ribofuranosyl)-4(1H)-pyrimidinone, 1. The hydroxy groups are protected as acetyl esters using acetic anhydride in pyridine. The N1 nitrogen atom is alkylated according to the procedure described in K. Muhlegger, et al. 1996, WO 96/28640, using methyl acrylate in triethyl amine. The ester, 8 is converted to amide, 9, using ethylene diamine. The biotin labeled compound is prepared by reacting amide, 9, with biotin-dPEG4™-NHS (purchased from Quanta Biodesign). Alternatively, amide 9 is reacted with 5-carboxyfluorescein-NHS. The product is converted into a 5'-triphosphate using standard phosphorylation conditions to afford, respectively, nucleic acid labeling compounds 10 and 11.

Figure 6:
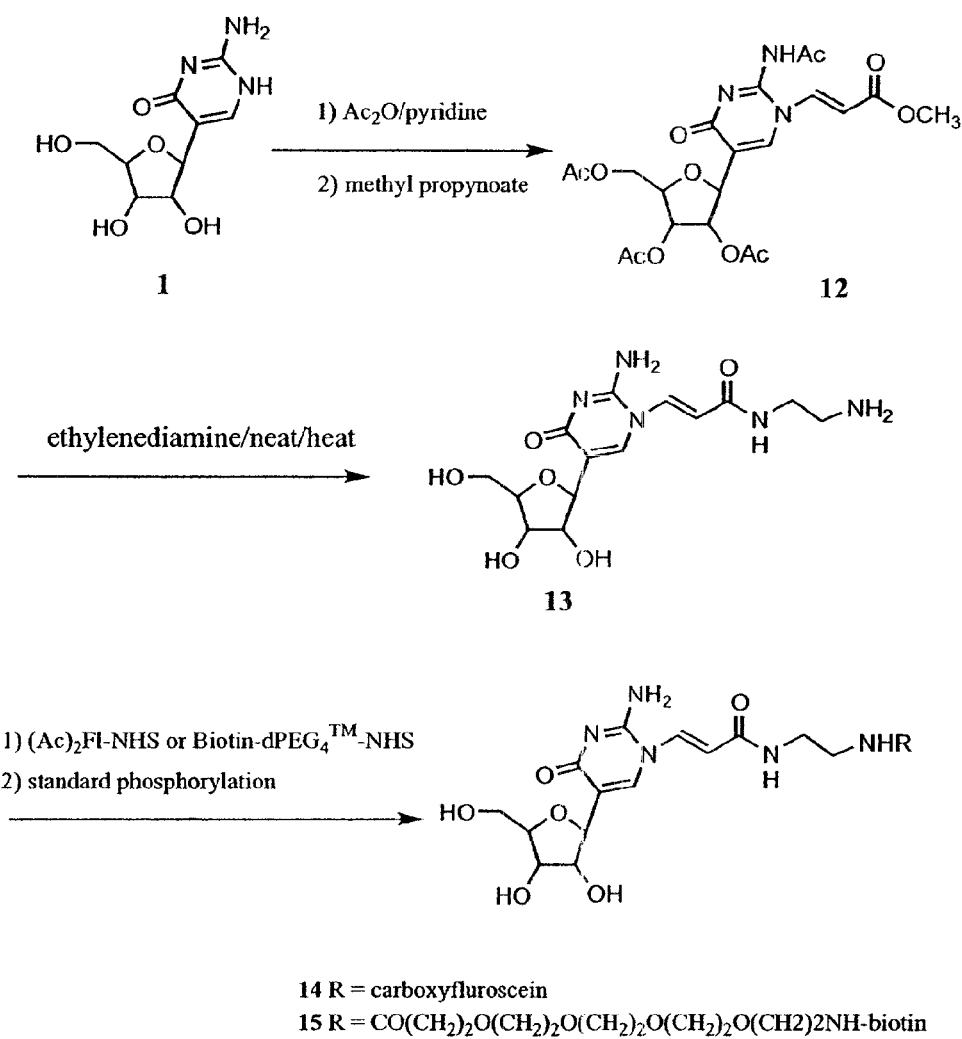

FIG. 6 illustrates a synthetic route to nucleic acid labeling compounds, 14 and 15, starting from 2-amino-5-(β-D-ribofuranosyl)-4(1H)-pyrimidinone, 1. The hydroxy groups are protected as acetyl esters using acetic anhydride in pyridine. The N1 nitrogen atom is alkylated according to the procedure described in *Tet Lett* 1995 36, 3261, using methyl propynoate. The ester, 12 is converted to amide, 9, using ethylene diamine. The biotin labeled compound is prepared by reacting amide, 9, with biotin-dPEG4™-NHS (purchased from Quanta Biodesign). Alternatively, amide 9 is reacted with 5-carboxyfluorescein-NHS. The product is converted into a 5'-triphosphate using standard phosphorylation conditions to afford, respectively, nucleic acid labeling compounds 14 and 15.

Figure 7:
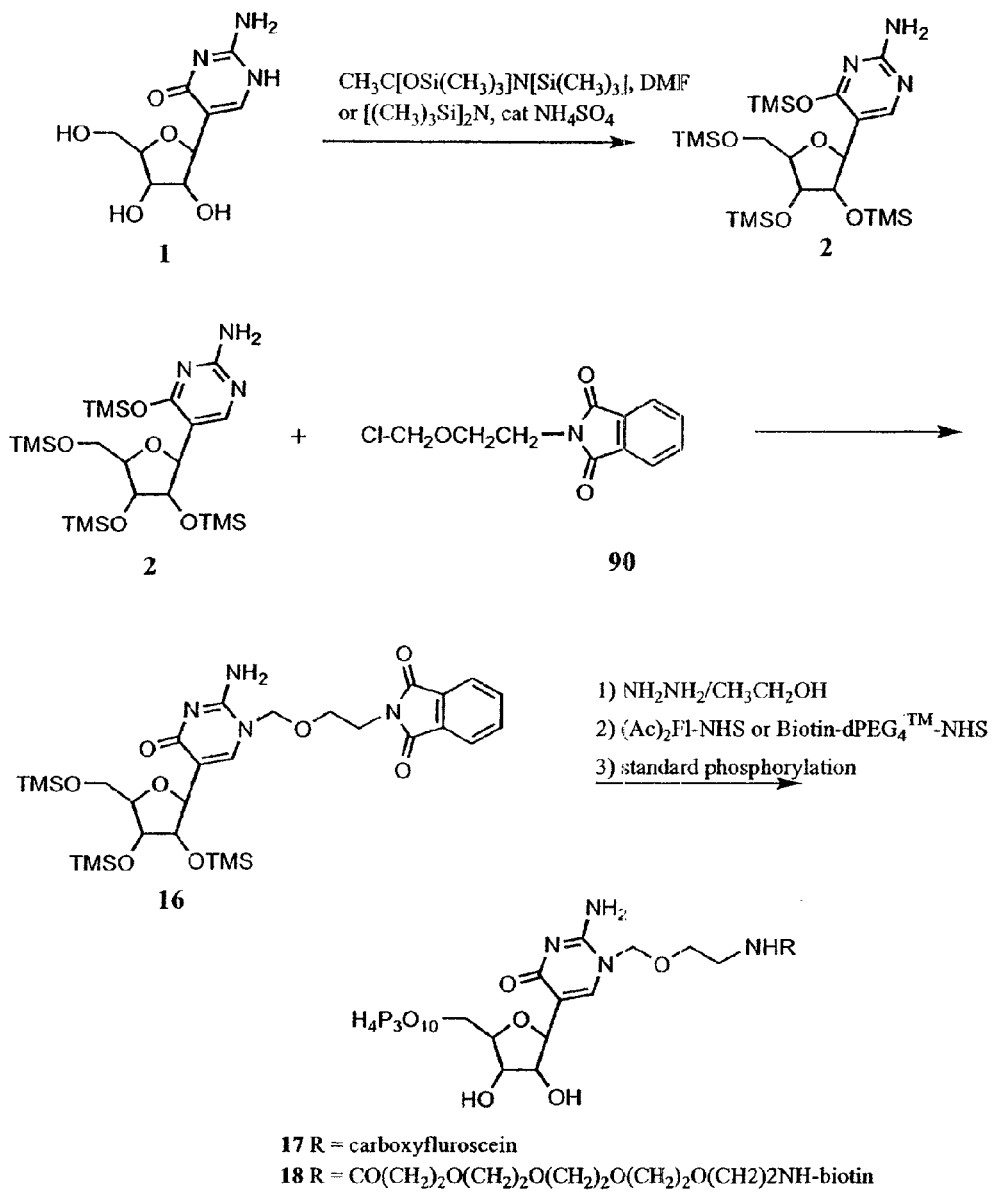

FIG. 7 illustrates a synthetic route to nucleic acid labeling compounds, 17 and 18, starting from 2-amino-5-(β-D-ribofuranosyl)-4(1H)-pyrimidinone, 1. The hydroxy groups are protected as the trimethyl silylethers according to the procedure described in *J. Antibiot.* 1977, 30, 129. The N1 nitrogen atom is alkylated, using 2-(2-chloromethoxy-ethyl)-isoindole-1,3-dione, according to the procedure described in *Chemo* 1985, 31, 151. The product, 16 is treated with hydrazine in ethanol to remove the protecting groups. The biotin labeled compound is prepared by reacting the ether-amine with biotin-dPEG4™-NHS (purchased from Quanta Biodesign) using standard conditions. Alternatively, the ether-amine is reacted with (Ac)₂Fl-NHS using standard conditions. The product is converted into a 5'-triphosphate using standard phosphorylation conditions to afford, respectively, nucleic acid labeling compounds 17 and 18.

Figure 8:
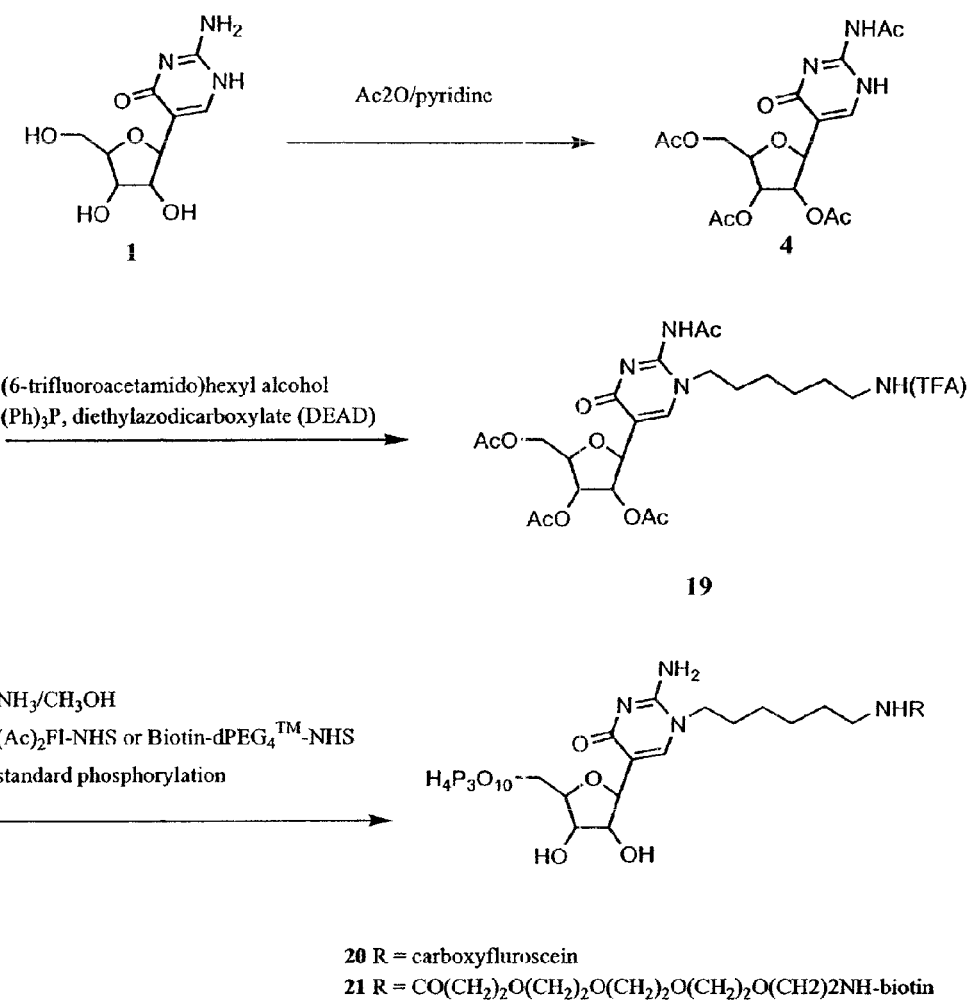

FIG. 8 illustrates a synthetic route to nucleic acid labeling compounds, 20 and 21, starting from 2-amino-5-(β-D-ribofuranosyl)-4(1H)-pyrimidinone, 1. The hydroxy groups are protected as acetyl esters using acetic anhydride in pyridine. The N1 nitrogen atom is alkylated using (6-trifluoroacetamido)hexyl alcohol in the presence of triphenyl phosphane ((Ph)₃P), and diethylazodicarboxylate (DEAD), according to the procedure described in Brossette, T. et al., *J. Org. Chem.* 1999, 64, 5083 and *Nuclesies, Nucleotides and Nucleic Acids* 2000, 19, 867. The N1 nitrogen atom is alkylated using (6-trifluoroacetamido)hexyl alcohol according to the procedure described in *J. Antibiot.* 1977, 30, 129. The protecting groups are removed to provide a compound having free amine and alcohol groups, using ammonia in methanol. The biotin labeled compound is prepared by reacting the ether-amine with biotin-dPEG4™-NHS (purchased from Quanta Biodesign) using standard conditions. Alternatively, the ether-amine is reacted with (Ac)₂Fl-NHS using standard conditions. The product is converted into a 5'-triphosphate using standard phosphorylation conditions to afford, respectively, nucleic acid labeling compounds 20 and 21.

Figure 9:
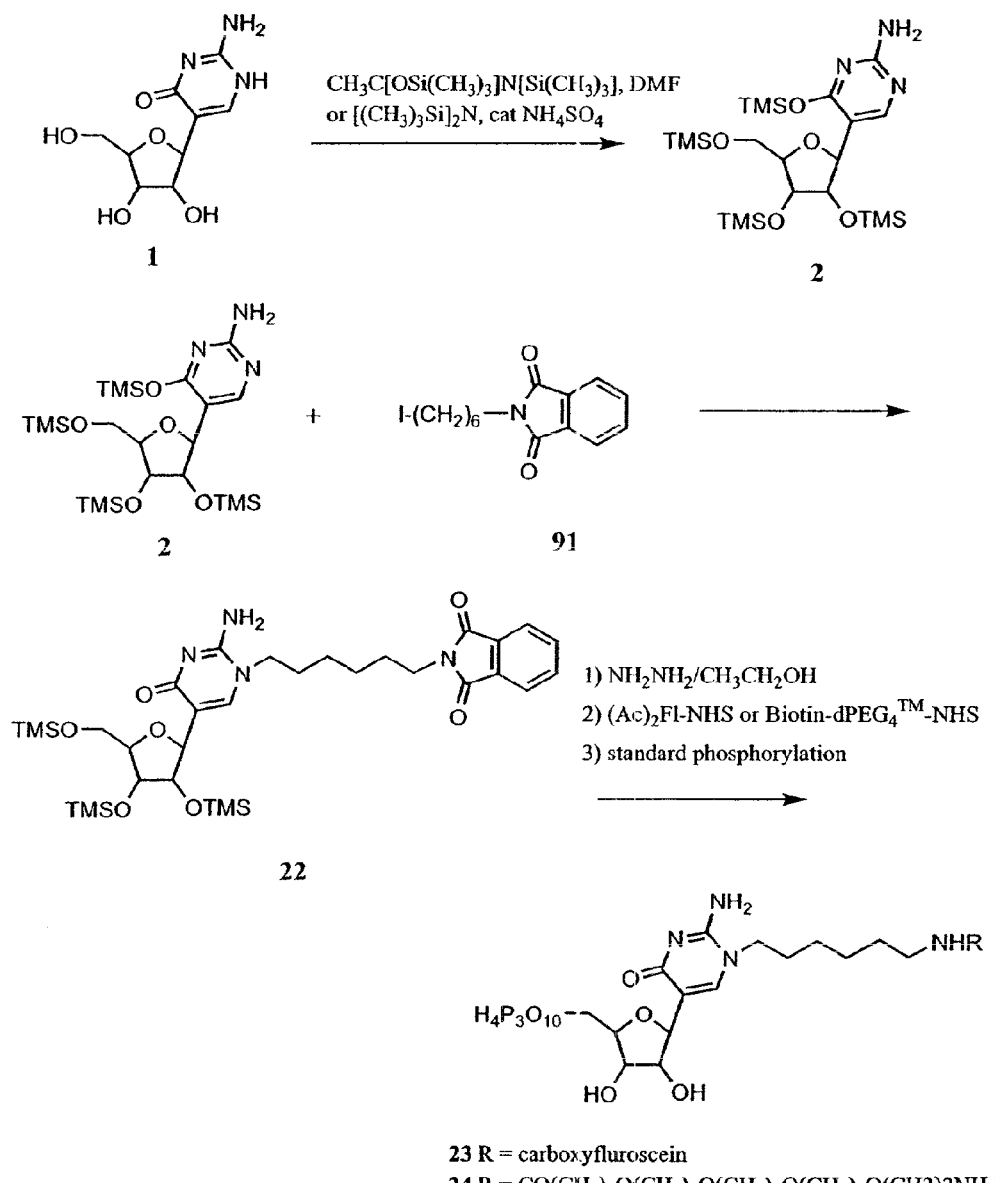

FIG. 9 illustrates a synthetic route to nucleic acid labeling compounds, 23 and 24, starting from 2-amino-5-(β-D-ribofuranosyl)-4(1H)-pyrimidinone, 1. The hydroxy groups are protected as acetyl esters using acetic anhydride in pyridine. The N1 nitrogen atom is alkylated using 2-(6-iodo-hexyl)-isoindole-1,3-dione according to the procedure described in *J. Antibiot.* 1977, 30, 129. The product, 22 is treated with hydrazine in ethanol to remove the protecting groups. The biotin labeled compound is prepared by reacting the free amine with biotin-dPEG4™-NHS (purchased from Quanta Biodesign) using standard conditions. Alternatively, the ether-amine is reacted with (Ac)₂Fl-NHS using standard conditions. The product is converted into a 5'-triphosphate using standard phosphorylation conditions to afford, respectively, nucleic acid labeling compounds 23 and 24.

Figure 10:
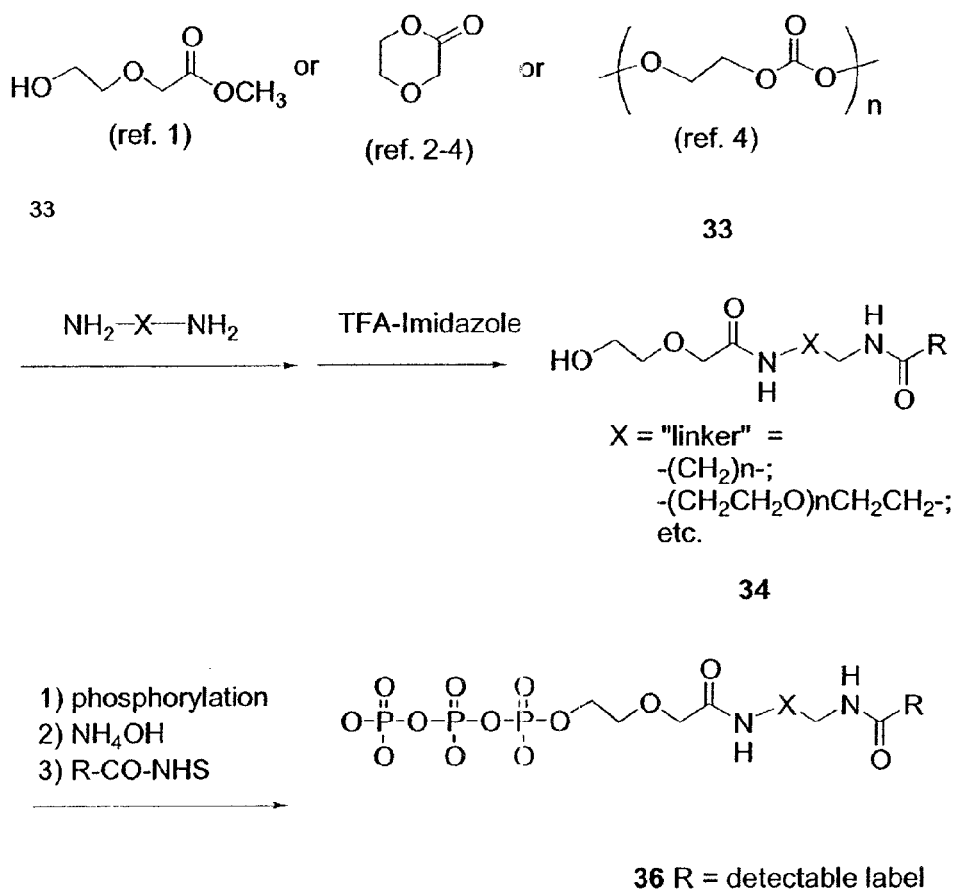

FIG. 10 illustrates a synthetic route to nucleic acid labeling compounds, 36, starting from [1,4]Dioxan-2-one. Shahi, S. P., et al., *J. Org. Chem.* (1999), 64: 4509-11. Nishimura. T, et al., *J. Org. Chem.* 1999, 64: 6750-55, Nishida H, et al., *J. Polym. Sci.* 2000, 38: 1560-67; (2-Hydroxy-ethoxy)-acetic acid methyl ester, Kitano, M.; and Ohashi, N., EP 787728 A1 (1997), or a polymer thereof, Nishida H, at al. *J. Polym. Sci.*, (2000), 38: 1560-67, 33. The compound is reacted with a diamine having a suitable linker moiety, e.g., a polyethylene oxide, alkylene, a combination there of and the like. The labeled compound is prepared by reacting the ether-amine with a suitable labeling compound using standard conditions. The product is convened into a 5'-triphosphate using standard phosphorylation conditions to afford, respectively, nucleic acid labeling compound 36.

Nucleic Acid Labeling

Nucleic acids can be isolated from a biological sample or synthesized, on a solid support or in solution for example, according to methods known to those of skill in the art. As used herein, there is no limitation on the length or source of the nucleic acid used in a labeling process. Exemplary methods of nucleic acid isolation and purification are described in Theory and Nucleic Acid Preparation. In *Laboratory Techniques in Biochemistry and Molecular Biology: Hybridization With Nucleic Acid Probes*; P. Tijssen. Ed.; Part 1; Elsevier; N.Y. 1993. A preferred method of isolation involves an acid guanidinium-phenol-chloroform extraction followed by oligo dT column chromatography or (dT)n magnetic bead use. Sambrook et al. *Molecular Cloning: A Laboratory Manual*, 2nd ed.; Cold Spring Harbor Laboratory, 1989; Vols. 1-3; and *Current Protocols in Molecular Biology*; F. Ausubel et al. Eds.; Greene Publishing and Wiley Interscience; N.Y. 1987.

In certain cases, the nucleic acids are increased in quantity through amplification. Suitable amplification methods include, but are not limited to the following examples; polymerase chain reaction (PCR) (Innis, et al. *PCR Protocols, A guide to Methods and Application*; Academic Press; San Diego, 1990); ligase chain reaction (LCR) (Wu and Wallace. *Genomics* 1989, 4, 560; Landgren, et al. *Science* 1988, 241, 1077; and Barringer, et al. *Gene* 1990, 89, 117); transcription amplification (Kwoh et al. *Proc. Natl. Acad. Sci. USA* 1989, 86, 1173); and self-sustained sequence replication (Guatelli, et al. *Proc. Nat. Acad. Sci. USA* 1990, 87, 1874).

The nucleic acid labeling compound can be incorporated into a nucleic acid using a number of methods. For example, it can be directly attached to an original nucleic acid sample (e.g., MRNA, polyA mRNA, cDNA) or to an amplification product. Methods of attaching a labeling compound to a nucleic acid include, without limitation, nick translation, 3-end-labeling, ligation, in vitro transcription (IVT) or random priming. Where the nucleic acid is an RNA, a labeled riboligonucleotide is ligated, for example, using an RNA ligase such as T4 RNA Ligase. In *The Enzymes*: Uhlenbeck and Greensport, Eds.; Vol. XV, Part B, pp. 31-58; and, Sambrook et al, pp. 5.66-5.69. Terminal transferase is used to add deoxy-, dideoxy- or ribonucleoside triphosphates (dNTPs, ddNTPs or NTPs), for example, where the nucleic acid is single stranded DNA.

The labeling compound can also be incorporated at an internal position of a nucleic acid. For example, PCR in the presence of a labeling compound provides an internally labeled amplification product. See, e.g. Yu et al. *Nucleic Acids Research* 1994, 22, 3226-3232. Similarly, IVT in the presence of a labeling compound can provide an internally labeled nucleic acid.

Probe Hybridization

The nucleic acid to which the labeling compound is attached can be detected after hybridization with a nucleic acid probe. Alternatively, the probe can be labeled, depending upon the experimental scheme preferred by the user. The probe is a nucleic acid, or a modified nucleic acid, that is either attached to a solid support or is in solution. It is complementary in structure to the labeled nucleic acid with which it hybridizes. The solid support is of any suitable material, including polystyrene based beads and glass chips. In a preferred embodiment, the probe or target nucleic acid is attached to a glass chip, such as a GeneChip® product (Affymetrix, Inc. Santa Clara, Calif.). See International Publication Nos. WO 97/10365, WO 97/29212, WO 97/27317, WO 95/11995, WO 90/15070, and U.S. Pat. Nos. 5,744,305 and 5,445,934 which are hereby incorporated by reference.

Because probe hybridization is often a step in the detection of a nucleic acid, the nucleic acid labeling compound must be of a structure that does not substantially interfere with that process. The steric and electronic nature of the labeling compound, therefore, is compatible with the binding of the attached nucleic acid to a complementary structure.

EXAMPLES

The following examples are offered to illustrate, but not to limit, the present invention.

General Experimental Details

Reagents were purchased from Aldrich Chemical Company (Milwaukee, Wis.) in the highest available purity. All listed solvents were anhydrous. Intermediates were characterized by $^1$H NMR and mass spectrometry.

Example 1

Synthesis of Fluorescein Derivatives of 2'-amino-2'-deoxyuridine Triphosphate and 3'-amino-3'-deoxythymidinetriphosphate (Scheme 1)

To 0.5 umoles (50 uL of a 10 mM solution) of the amino nucleotide triphosphate (1 or 2) in a 0.5 ml ependorf tube was added 25 ul of a 1 M aqueous solution of sodium borate, pH 8, 87 uL of methanol, and 88 uL (10 umol, 20 equiv) of a 100 mM solution of 5-carboxyfluorescein —X—NHS ester in methanol. The mixture was vortexed briefly and allowed to stand at room temperature in the dark for 15 hours. The sample was then purified by ion-exchange HPLC to afford the fluoresceinated derivatives 3 or 4 in about 78-84% yield. Relative efficiencies of incorporation of these compounds by TdT are shown in Table 1.

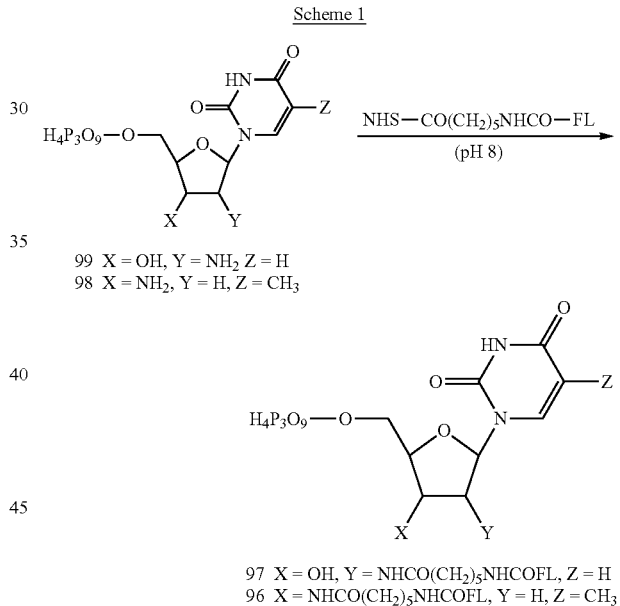

Scheme 1

TABLE 1

Incorporation of triphosphate compounds by TdT.

| TdT Labeling Labeling Efficiencies | | | % Labeled | |
|---|---|---|---|---|
| X (3') | Y (2') | B (1'b) | 40U | 160U |
| OH | H | uracil | 100.0 | 100.0 |
| NH2 | H | thymine | 100 | 100 |

TABLE 1-continued

Incorporation of triphosphate compounds by TdT.

| TdT Labeling Labeling Efficiencies | | | % Labeled | |
|---|---|---|---|---|
| X (3') | Y (2') | B (1'b) | 40U | 160U |
| NHCO(CH2)5NH—(CO—FL) | H | thymine | 1.3 | 2.2 |
| OH | NH2 | uracil | 65 | 95 |
| OH | NHCO(CH2)5NH—(CO—FL) | uracil | 3.0 | 6.6 |
| OH | O(CH2)6NH—(CO—FL) | uracil | 2.5 | 7.0 |
| OH | O(CH2)6NHCO—(CH2)5—NHCO-Biotin | uracil | 15.0 | 17.0 |
| OH | NH(CH2)5CH3 | uracil | 4.5 | 5.0 |

Example 2

Synthesis of N1-labeled 2-Amino-5-(β-D-ribofuranosyl)-4(1H)-pyrimidinone

Figure 3A:
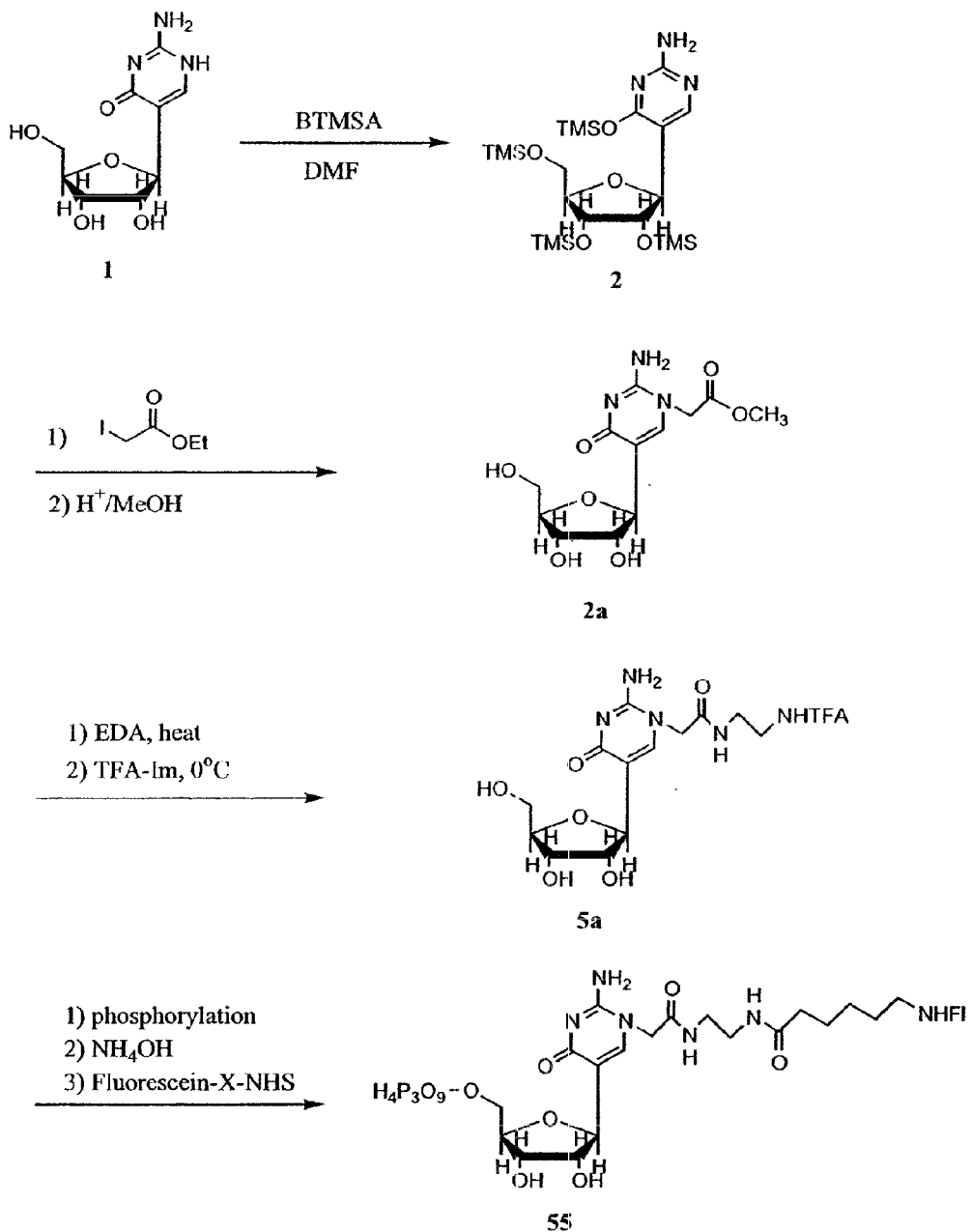

Synthesis of the N1-labeled 2-amino-5-(β-D-ribofuranosyl)-4(1H)-pyrimidinone, 55, involved alkylation at N1 using conditions similar to those described by Muehlegger, et al. (WO 96/2640) for the N1-alkylation of pyrazalo-[4,3-d]pyrimidines (FIG. 3A).

Example 3

Synthesis of N-(6-(fluorescein-5-carboxamido)hexanoyl)-morpholino Uridine Triphosphate (Scheme 2)

Morpholino-uracil tosylate salt 25 (30 mg) was co-evaporated with pyridine (3×3 ml) and dissolved in 2 ml of pyridine and cooled to 0° C. Trifluoroacetic anhydride (30 uL) was added and stirred for 1 hour. The reaction was followed by HPLC until complete. The pyridine was removed and the residue was dissolved in 1 ml of water and filtered. The product was purified by HPLC on a Waters C-18 bondapak cartridge (Buffer: A=50 mM TEM pH 7.0; B=acetonitrile) using a gradient of 0-25% B in 30 minutes (retention time=22 min.). The product was desalted on a Sep-Pak cartridge and freeze-dried to give 151 mg of 26. Phosphorylation of 2 using the POCl3 method gave 27. The removal of the trifluoroacetyl group with conc. NH4OH at 50° C. for 30 min to provide the free amine, 28. Conjugation of 28 to 5-carboxyfluoroscein-aminocaproic acid N-hydroxysuccinimide (Fl-X—NHS) under standard conditions provided amide 29. The mass spectral and NMR data for compounds 25-29 were consistent with the proposed structures.

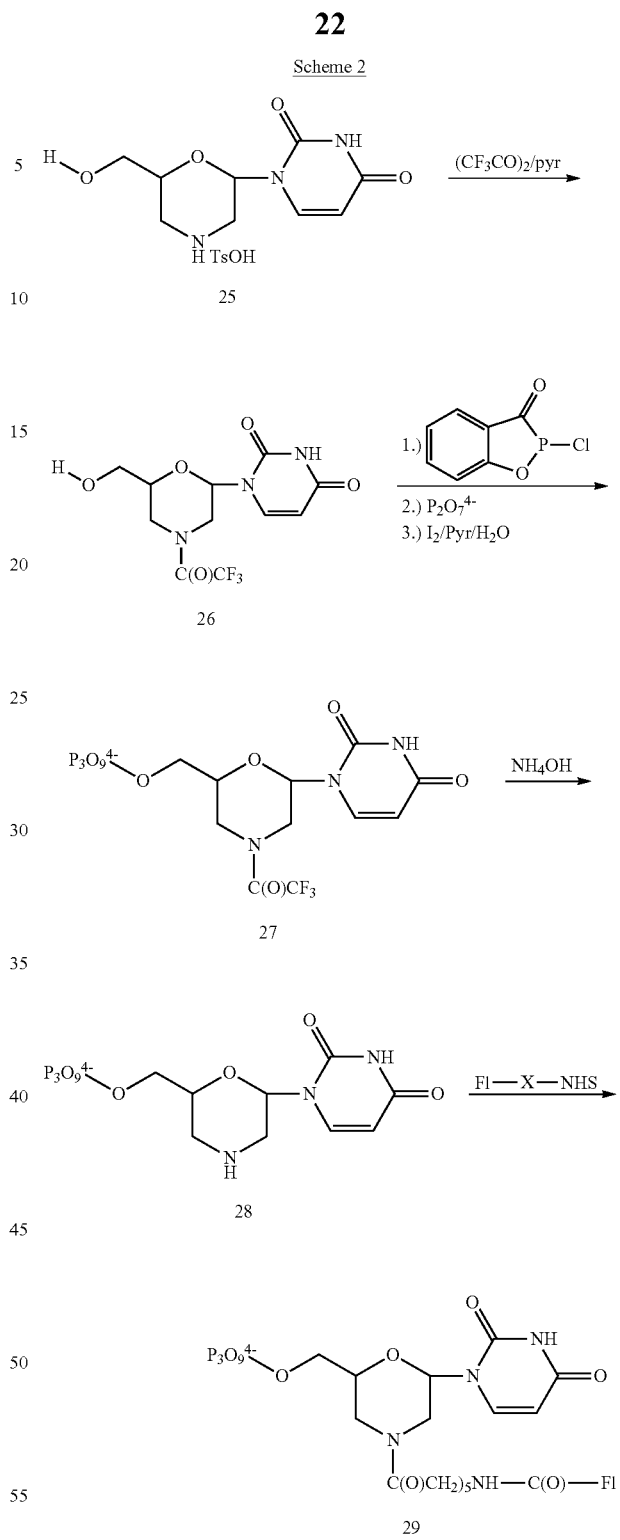

Scheme 2

Example 4

The compounds of the invention having general formulas I, IA IB, II, III, IIIA, IIIB, and IV as disclosed herein can be prepared using available reagents and procedures that are standard in the art. In addition, examples of these procedures are illustrated in FIGS. 2-10.

Example 5

Procedure for HPLC Analysis of Enzymatic Incorporation of Modified Nucleotides Reaction Conditions
TdT
3 uM $dT_{16}$ template
15(30) uM NTP
40 U TdT (Promega)
1× buffer, pH 7.5 (Promega)

Procedure; incubate 1 hr, at 37° C., then for 10 min, at 70° C., followed by the addition of EDTA (2 mM final concentration) in a volume of 50 uL HPLC Analysis Materials and Reagents 4.6 mm×250 mm Nucleopac PA-100 ion-exchange column (Dionex) buffer A: 20 mM NaOH (or 20 mM Tris pH 8, in the case of TdT incorporation of nucleotide triphosphates that are not dye-labeled) buffer B: 20 mM NaOH, 1M NaCl (or 20 mM Tris pH 8, 1M NaCl, in the case of TdT incorporation of nucleotide triphosphates that are not dye-labeled)

General Procedure

Dilute the reaction with 50 uL of buffer A. Inject 50 uL of this sample onto the HPLC column and fractionate using a gradient of 5 to 100% buffer B over 30 minutes at a flow rate of 1 mL/min. Detect the peaks simultaneously at 260 nm absorbance and the absorbance maximum of the dye (or the fluorescence emission maximum of the dye).

The incorporation efficiency is expressed as the fraction of oligonucleotide that is labeled. This number is determined by dividing the peak area measured at 260 nm absorbance of the labeled oligonucleotide by the sum of the peak areas of the unlabeled and labeled oligonucleotide. (The retention time of fluorescein-labeled $dT_{16}$ is on the order of 2 to 3 min, longer than the unlabeled $dT_{16}$.) The error in this type of assay is about 10%. The percentage labeling efficiency for 4 types of nucleic acid labeling compounds is shown below in Table 1.

Example 6

Labeled N-(2-hydroxyethoxy)ethyl 2-O-triphosphates (Scheme 3)

Compounds having general formula can be prepared using available reagents and procedures that are standard in the art. In addition, examples of these procedures are illustrated in Schemes 3 and FIG. 10.

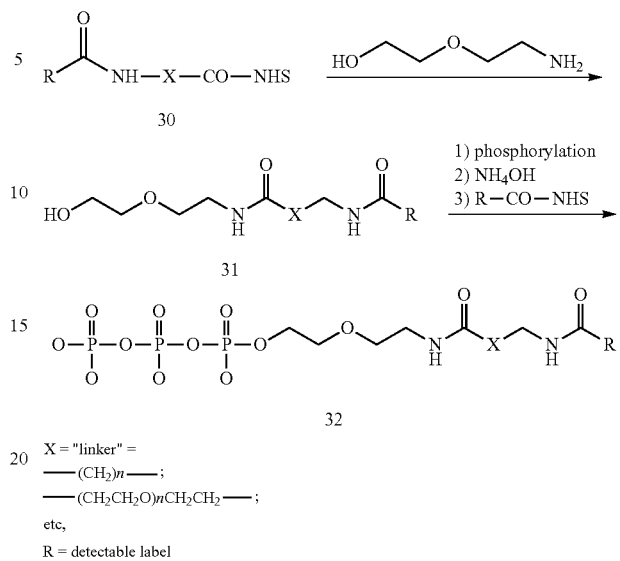

Example 6A

Labeled 2-(2-hydroxyethyl)acetamide 2-O-triphosphates (FIG. 10)

[1,4]Dioxan-2-one, (2-Hydroxy-ethoxy)-acetic acid methyl ester, or a polymer thereof, 33, is reacted with a diamine having a linker moiety, e.g., a polyethylene oxide, alkylene, a combination there of. The labeled compound is prepared by reacting the ether-amine with a suitable labeling compound using standard conditions. The product is converted into a 5'-triphosphate using standard phosphorylation conditions to afford, respectively, nucleic acid labeling compound 36.

Example 7

Synthesis of N-alkyl 2'-amino-2'-deoxyuridine Triphosphate (Scheme 4)

4,4-Diethoxy-butylamine is reacted with an activated N-labeled caproyl amine, 37 to provide the N-labeled diethoxy butyl caproyl amide, 38. The amide, 38, is reacted with aqueous hydrochloric acid (0.04 N) to produce the N-labeled aldehyde, the aldehyde is reacted with phosphorylated 1-(3-Amino-4-hydroxy-5-hydroxymethyl-tetrahydro-furan-2-yl)-H-pyrimidine-2,4-dione, 39, to furnish labeled N-alkyl 2'-amino-2'-deoxyuridine triphosphate, 40. The reaction is illustrated in Scheme 4.

Scheme 4

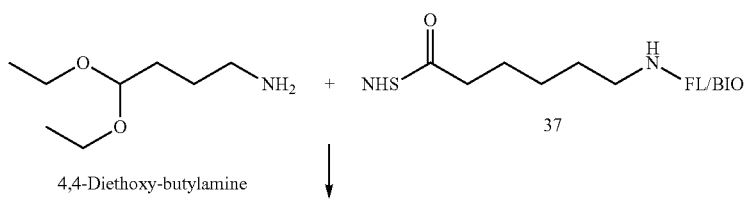

4,4-Diethoxy-butylamine

-continued

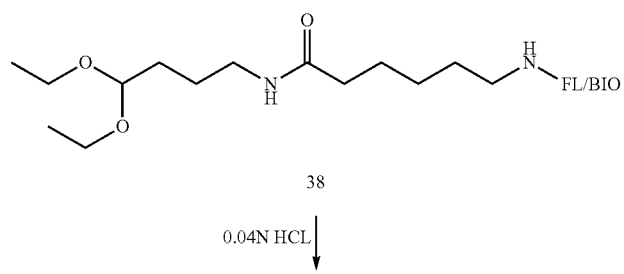

38

0.04N HCL ↓

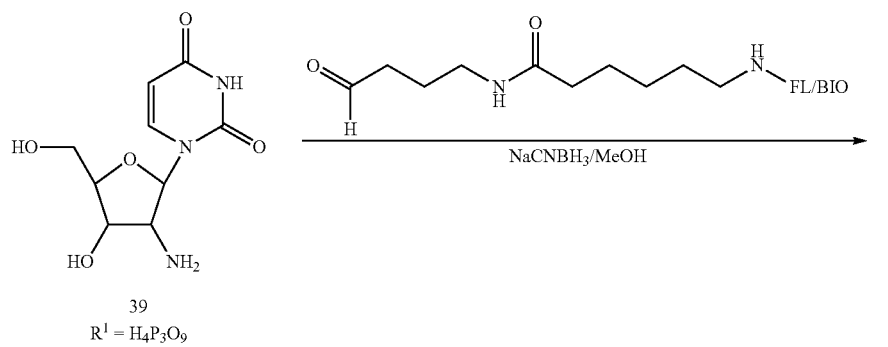

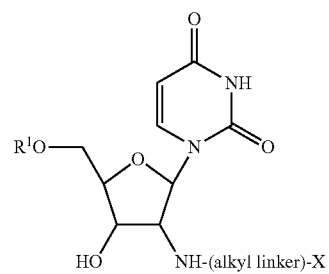

40
R¹ = H₄P₃O₉
X = Fluorescein, Biotin

Example 8

Synthesis of 2'-O-(6-(Fluorescein-5-carboxamido)hexyl)uridine 5'-O-triphosphate (Scheme 5)

The protected phthalimide, 41, (available from RI Chemicals, 500 mg), is reacted successively with a) hydrazine/ethanol, b) Trifluoroacetic acid-imidazole at 0° C. and c) Acetic acid/methanol to provide compound, 42. The alcohol-amine is converted into a 5'-triphosphate using standard phosphorylation conditions followed by conjugation to a label to afford, respectively, nucleic acid labeling compounds, 43.

Scheme 5

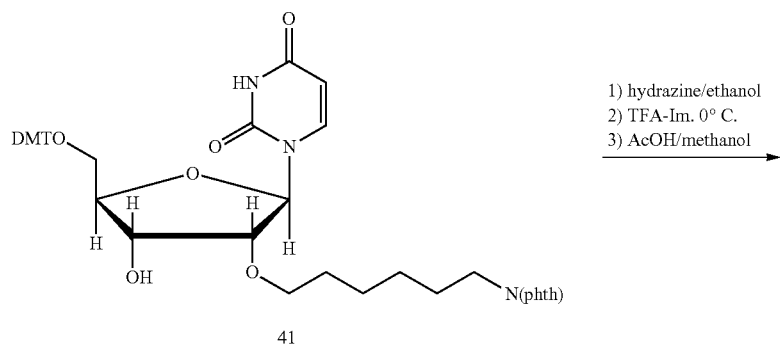

41

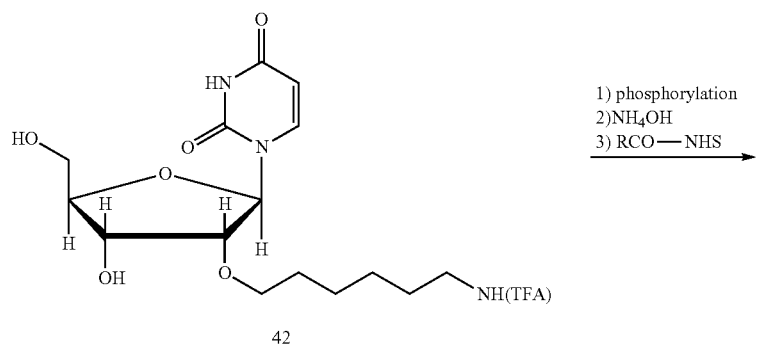

42

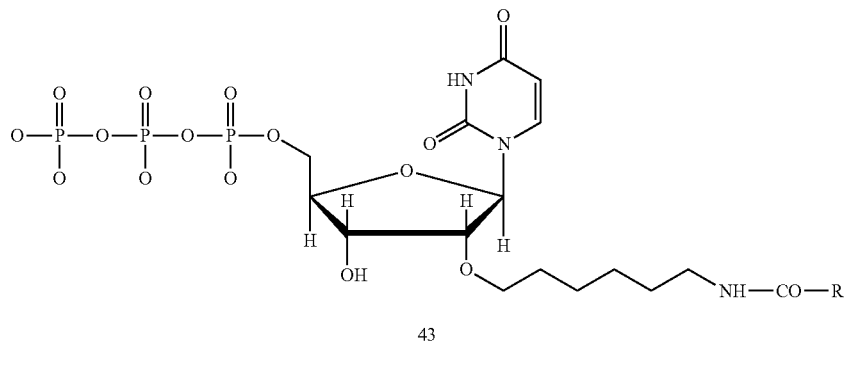

43

Example 9

Synthesis of 2'-S(N-(6-(Fluorescein-5-carboxamido)hexyl)aminoethyldithiouridine 5'-O-triphosphate (Scheme 6)

3-Hydroxy-2-hydroxymethyl-2,3,3a,9a-tetrahydro-furo[2',3';4,5]oxazolo[3,2-a]pyrimidin-6-one, 44, is treated with acetic anhydride in pyridine to protect the hydroxy groups. The protected compound, 45, is reacted with thioacetic acid/dioxane at 100° C., according to the procedure in J. Chem. Soc. Perkin Trans 1, 1997, 2587, the product is treated with ammonia provide thiol, 46. The thiol is reacted with disulfide, 99, to provide disulfide, 47, the disulvide is converted into a 5'-triphosphate using standard phosphorylation conditions followed by reaction with a labeled reagent to afford, respectively, nucleic acid labeling compounds, 43.

Scheme 6

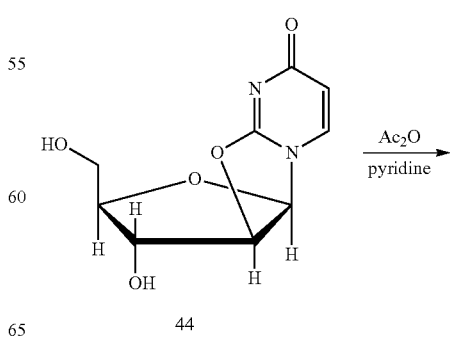

44

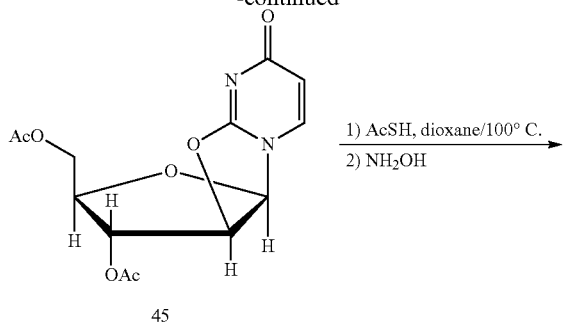

45

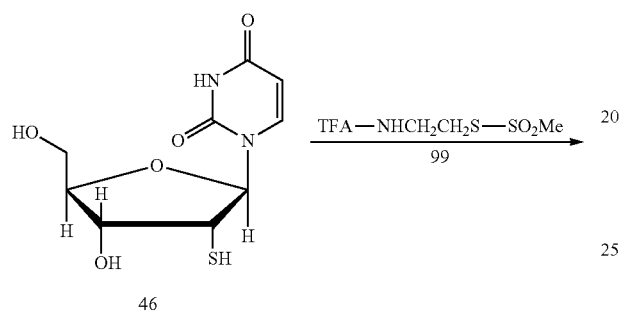

46

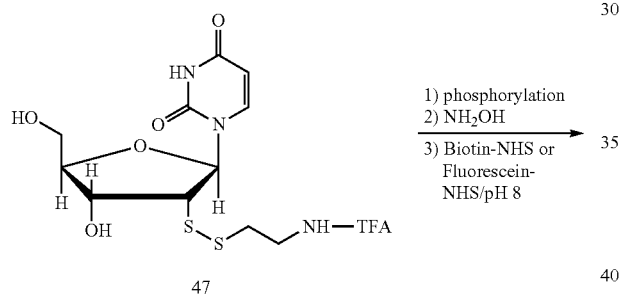

47

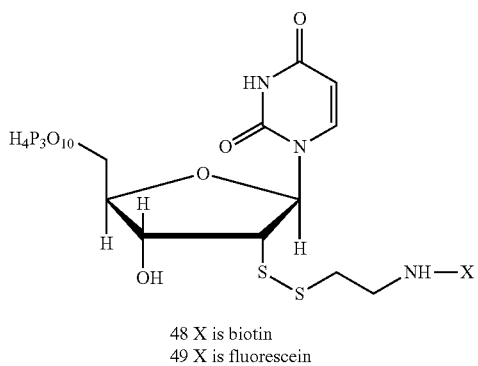

48 X is biotin
49 X is fluorescein

All patents, patent applications, and literature cited in the specification are hereby incorporated by reference in their entirely. In the case of any inconsistencies, the present disclosure, including any definitions therein will prevail.

The invention has been described with reference to various specific and preferred embodiments and techniques. However, it should be understood that many variations and modifications may be made while remaining within the spirit and scope of the invention.

The invention claimed is:

1. A nucleic acid labeling compound represented by the structure

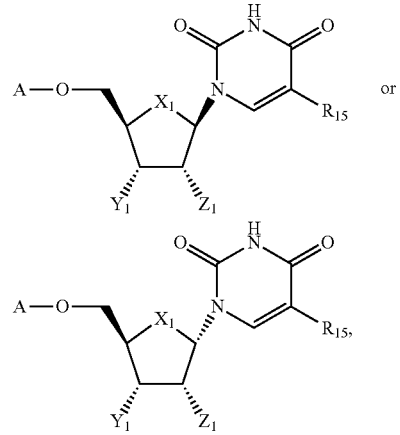

wherein:

A is hydrogen, monophosphate, diphosphate, triphosphate, α-thiotriphosphate, phosphoramidite, or H-phosphonate;

$X_1$ is O, S, $NR_1$, or $CHR_2$, wherein $R_1$ and $R_2$ are, independently, hydrogen, alkyl, or aryl;

$R_{15}$ is hydrogen, alkyl, or aryl;

$Y_1$ is hydrogen, $N_3$, F, $OR_9$, $SR_9$, or $NHR_9$, wherein $R_9$ is hydrogen, alkyl, or aryl;

$Z_1$ is hydrogen, $N_3$, F, $OR_9$, $SR_9$, or $NHR_{10}$, wherein $R_{10}$ is hydrogen, alkyl, or aryl;

one of $Y_1$ or $Z_1$ is a group having the formula —$X_2$L-M-Q;

$X_2$ is O, S, or $NR_{16}$, wherein $R_{16}$ is hydrogen, alkyl, or aryl;

L is a linker moiety that is sterically and electronically suitable for incorporation into a nucleic acid;

Q is a detectable moiety selected from the group consisting of biotin, carboxyfluorescein, colloidal gold, radiolabels, magnetic particles, fluorescent labels, chemiluminescent or bioluminescent labels, spin labels, dyes, and colored beads; and M is a connecting group comprising a structure that does not interfere with the nucleic acid labeling compound's function.

2. The nucleic acid labeling compound of claim 1, wherein:
L is selected from the group consisting of amido alkyl, functionalized alkyl, alkenyl alkyl, alkanoyl, and N-alkyl amido.

3. The nucleic acid labeling compound of claim 1, wherein:
M is selected from the group consisting of amino alkyl, —CO(CH$_2$)$_5$NH—, —CO—, —NH—, —CO(O)—, —CO(NH)—, —(CH$_2$)$_i$O—, —(CH$_2$)$_j$NH—, —C(O)(CH$_2$)$_h$O—, —CO(CH$_2$)$_5$NHCO(CH$_2$)$_5$NH—, —NH(CH$_2$CH$_2$O)$_k$NH—, and —CO(CH$_2$)$_5$—, wherein h, i, j, and k are independently integers from 1 to 5.

4. The nucleic acid labeling compound of claim 1, wherein:
$Y_1$ is selected from the group consisting of hydrogen, $OR_9$, wherein $R_9$ is hydrogen or alkyl, —$NR_{16}$-L-(M)$_m$-Q, wherein $R_{16}$ is hydrogen, alkyl, or aryl, —O-L-(M)$_m$-Q, and —S-L-(M)$_m$-Q.

5. The nucleic acid labeling compound of claim 1, wherein:
$Z_1$ is selected from the group consisting of hydrogen, $OR_{10}$, wherein $R_{10}$ is hydrogen or alkyl, —$NR_{16}$-L-(M)$_m$-Q, wherein $R_{16}$ is hydrogen or alkyl, —O-L-(M)$_m$-Q, and —S-L-(M)$_m$-Q.

6. The nucleic acid labeling compound of claim 1, wherein Q is:
- a fluorescent group which absorbs light with a wavelength above 300 nm, and emits light with a wavelength above 310 nm, or
- a fluorescent group which absorbs light with a wavelength above 400 nm, and emits light with a wavelength above 410 nm.

7. The nucleic acid labeling compound of claim 1, wherein:
A is H or $H_4O_9P_3$—;
$X_1$ is O;
$Y_1$ is hydrogen, $OR_9$, wherein $R_9$ is hydrogen or alkyl, or —$NR_{16}$-L-(M)$_m$-Q, wherein $R_{16}$ is hydrogen, alkyl, or aryl;
$Z_1$ is hydrogen, $OR_{10}$, wherein $R_{10}$ is hydrogen or alkyl, or —$NR_{16}$-L-(M)$_m$-Q, wherein $R_{16}$ is hydrogen or alkyl;
L is selected from the group consisting of amido alkyl, functionalized alkyl, alkenyl alkyl, alkanoyl, and N-alkyl amido;
$R_{15}$ is hydrogen or alkyl;
M is selected from the group consisting of amino alkyl, —$CO(CH_2)_5NH$—, —CO—, —NH—, —CO(O)—, —CO(NH)—, —$(CH_2)_iO$—, —$(CH_2)_jNH$—, —$C(O)(CH_2)_hO$—, —$CO(CH_2)_5NHCO(CH_2)_5NH$—, —$NH(CH_2CH_2O)_kNH$—, and —$CO(CH_2)_5$—, wherein h, i, j, and k are independently integers from 1 to 5; and
m is an integer from 1 to 15.

8. The nucleic acid labeling compound of claim 7, wherein:
L is N-alkyl amido; and
M is —$CH_2$—$NR_3$—, wherein $R_3$ is hydrogen or alkyl.

9. The nucleic acid labeling compound of claim 7, wherein:
$Y_1$ is hydrogen or OH;
$Z_1$ is —NH-L-(M)$_m$-Q;
L is —$(CH_2)_nNHC(O)$—, where n is an integer from 1 to 10;
M is —$NH(CH_2)_p$—, where p is an integer from 1 to 10;
$R_{15}$ is hydrogen or methyl; and
Q is biotin or a carboxyfluorescein.

10. The nucleic acid labeling compound of claim 9, wherein:
$Y_1$ is OH;
$R_{15}$ is hydrogen or methyl;
-L-(M)$_m$- is —$(CH_2)_4NH$—$C(O)(CH_2)_5NH$—; and
Q is biotin or a carboxyfluorescein.

11. The nucleic acid labeling compound of claim 7, wherein:
$Y_1$ is —NH-L-(M)$_m$-Q;
$Z_1$ is hydrogen or OH;
L is selected from the group consisting of amido alkyl, functionalized alkyl, alkenyl alkyl, alkanoyl, and N-alkyl amido;
M is —$NH(CH_2)_p$—, where p is an integer from 1 to 10;
$R_{15}$ is hydrogen or methyl; and
Q is biotin or a carboxyfluorescein.

12. The nucleic acid labeling compound of claim 7, wherein:
A is H or $H_4O_9P_3$—;
$X_1$ is O;
$Y_1$ is hydrogen, $OR_9$, wherein $R_9$ is hydrogen or alkyl, or —O-L-(M)$_m$-Q;
$Z_1$ is hydrogen, $OR_{10}$, wherein $R_{10}$ is hydrogen or alkyl, or —O-L-(M)$_m$-Q;
L is alkylene; and
m is an integer from 1 to 10.

13. The nucleic acid labeling compound of claim 12, wherein:
$Y_1$ is hydrogen or OH;
$Z_1$ is —O-L-(M)$_m$-Q;
L is —$(CH_2)_n$—, where n is an integer from 1 to 12;
M is selected from the group consisting of amino alkyl, —$CO(CH_2)_5NH$—, —CO—, —NH—, —CO(O)—, —CO(NH)—, —$(CH_2)_iO$—, —$(CH_2)_jNH$—, —$C(O)(CH_2)_hO$—, —$CO(CH_2)_5NHCO(CH_2)_5NH$—, —$NH(CH_2CH_2O)_kNH$—, and —$CO(CH_2)_5$—, wherein h, i, j, and k are independently integers from 1 to 5;
$R_{15}$ is hydrogen or methyl; and
Q is biotin or a carboxyfluorescein.

14. The nucleic acid labeling compound of claim 13, wherein:
M is —NH—.

15. The nucleic acid labeling compound of claim 14, wherein:
$Y_1$ is OH;
$R_{15}$ is hydrogen or methyl;
-L-(M)$_m$- is —$(CH_2)_6$—NH—; and
Q is biotin or a carboxyfluorescein.

16. The nucleic acid labeling compound of claim 7, wherein:
$Y_1$ is —O-L-(M)$_m$-Q;
$Z_1$ is hydrogen or OH;
L is —$(CH_2)_n$—, where n is an integer from 1 to 12;
M is selected from the group consisting of amino alkyl, —$CO(CH_2)_5NH$—, —CO—, —NH—, —CO(O)—, —CO(NH)—, —$(CH_2)_iO$—, —$(CH_2)_jNH$—, —$C(O)(CH_2)_hO$—, —$CO(CH_2)_5NHCO(CH_2)_5NH$—, —$NH(CH_2CH_2O)_kNH$—, and —$CO(CH_2)_5$—, wherein h, i, j, and k are independently integers from 1 to 5;
$R_{15}$ is hydrogen or methyl; and
Q is biotin or a carboxyfluorescein.

17. The nucleic acid labeling compound of claim 16, wherein:
$Z_1$ is OH;
$R_{15}$ is hydrogen or methyl;
-L-(M)$_m$- is —$(CH_2)_6$—NH—; and
Q is biotin or a carboxyfluorescein.

18. The nucleic acid labeling compound of claim 7, wherein:
A is H or $H_4O_9P_3$—;
$X_1$ is O;
$Y_1$ is hydrogen, $OR_9$, wherein $R_9$ is hydrogen or alkyl, or —S-L-(M)$_m$-Q;
$Z_1$ is hydrogen, $OR_{10}$, wherein $R_{10}$ is hydrogen or alkyl, or —S-L-(M)$_m$-Q;
L is alkylene; and
m is an integer from 1 to 10.

19. The nucleic acid labeling compound of claim 18, wherein:
$Y_1$ is hydrogen or OH;
$Z_1$ is —S-L-(M)$_m$-Q;
L is —S—$(CH_2)_n$—, where n is an integer from 1 to 10;
M is selected from the group consisting of amino alkyl, —$CO(CH_2)_5NH$—, —CO—, —NH—, —CO(O)—, —CO(NH)—, —$(CH_2)_iO$—, —$(CH_2)_jNH$—, —$C(O)(CH_2)_hO$—, —$CO(CH_2)_5NHCO(CH_2)_5NH$—, —$NH(CH_2CH_2O)_kNH$—, and —$CO(CH_2)_5$—, wherein h, i, j, and k are independently integers from 1 to 5;
$R_{15}$ is hydrogen or methyl; and
Q is biotin or a carboxyfluorescein.

20. The nucleic acid labeling compound of claim 19, wherein:
$Y_1$ is OH;
$R_{15}$ is hydrogen or methyl;
-L-(M)$_m$- is —S—$(CH_2)_2$—NH—; and
Q is biotin or a carboxyfluorescein.

21. The nucleic acid labeling compound of claim 7, wherein:

$Y_1$ is —S-L-(M)$_m$-Q;

$Z_1$ is hydrogen or OH;

L is —S—(CH$_2$)$_n$—, where n is an integer from 1 to 10;

M is selected from the group consisting of amino alkyl, —CO(CH$_2$)$_5$NH—, —CO—, —NH—, —CO(O)—, —CO(NH)—, —(CH$_2$)$_i$O—, —(CH$_2$)$_j$NH—, —C(O)(CH$_2$)$_h$O—, —CO(CH$_2$)$_5$NHCO(CH$_2$)$_5$NH—, —NH(CH$_2$CH$_2$O)$_k$NH—, and —CO(CH$_2$)$_5$—, wherein h, i, j, and k are independently integers from 1 to 5;

$R_{15}$ is hydrogen or methyl; and

Q is biotin or a carboxyfluorescein.

22. The nucleic acid labeling compound of claim 21, wherein:

$Z_1$ is OH;

$R_{15}$ is hydrogen or methyl;

-L-(M)$_m$- is —S—(CH$_2$)$_2$—NH—; and

Q is biotin or a carboxyfluorescein.

23. A nucleic acid derivative produced by the process of:

attaching at least one nucleic acid to a support; and coupling the at least one nucleic acid to the nucleic acid labeling compound of claim 1.

24. The nucleic acid derivative produced by the process of claim 23, wherein either a terminal transferase or a ligase performs the coupling step.

25. A hybridization product, comprising the nucleic acid derivative of claim 23 bound to a complementary probe.

26. The hybridization product of claim 25, wherein the complementary probe is attached to a glass chip.

* * * * *